(12) United States Patent
Carter et al.

(10) Patent No.: US 7,560,232 B2
(45) Date of Patent: Jul. 14, 2009

(54) METHODS OF CAPTURING, DETECTING AND QUANTIFYING RNA:DNA HYBRIDS AND A MODIFIED RNASE H USEFUL THEREIN

(75) Inventors: Richard Carter, Newark, DE (US); Martin Rosenburg, Madison, WI (US); Daniel R. Gentry, Pottstown, PA (US); Nigel Grinter, Buffalo Grove, IL (US)

(73) Assignee: Promega Corporation, Madison, WI (US)

( * ) Notice: Subject to any disclaimer, the term of this patent is extended or adjusted under 35 U.S.C. 154(b) by 275 days.

(21) Appl. No.: 10/742,355

(22) Filed: Dec. 18, 2003

(65) Prior Publication Data

US 2004/0229242 A1 Nov. 18, 2004

Related U.S. Application Data

(60) Provisional application No. 60/435,136, filed on Dec. 19, 2002.

(51) Int. Cl.
*C12Q 1/68* (2006.01)
*C07K 14/00* (2006.01)

(52) U.S. Cl. .......................................... 435/6; 530/350
(58) Field of Classification Search ........................ None
See application file for complete search history.

(56) References Cited

U.S. PATENT DOCUMENTS

| | | | |
|---|---|---|---|
| 4,743,535 A | | 5/1988 | Carrico |
| 4,978,608 A | * | 12/1990 | Kung et al. ..................... 435/6 |
| 5,405,776 A | | 4/1995 | Kotewicz et al. |
| 5,668,005 A | | 9/1997 | Kotewicz et al. |
| 5,843,660 A | * | 12/1998 | Schumm et al. ................ 435/6 |
| 5,859,227 A | * | 1/1999 | Giordano et al. ........... 536/24.1 |
| 5,994,079 A | | 11/1999 | De La Rosa et al. |
| 6,043,038 A | | 3/2000 | Sivaraja et al. |
| 6,232,068 B1 | * | 5/2001 | Linsley et al. ................... 435/6 |
| 6,277,579 B1 | | 8/2001 | Lazar et al. |
| 6,573,045 B1 | * | 6/2003 | Karn et al. ...................... 435/6 |
| 6,686,151 B1 | | 2/2004 | Lazar et al. |
| 7,083,926 B2 | | 8/2006 | Rossi et al. |
| 2001/0044145 A1 | | 11/2001 | Monia et al. |
| 2002/0090617 A1 | | 7/2002 | Harbron |
| 2003/0064394 A1 | * | 4/2003 | Ohtake et al. .................. 435/6 |

FOREIGN PATENT DOCUMENTS

| | | |
|---|---|---|
| EP | 84114442.1 | 11/1984 |
| EP | 89109006.0 | 10/1989 |
| EP | 90314249.5 | 7/1991 |
| WO | WO 9719192 A1 * | 5/1997 |
| WO | WO 2004/0570116 A3 | 7/2004 |

OTHER PUBLICATIONS

Tsunaka et al. "Strong nucleic acid binding to the *Escherichia coli* RNase HI mutant with two arginine residues at the active site" Biochim Biophys Acta. May 5, 2001;1547(1):135-42).*
Haruki et al. ("Kinetic and stoichiometric analysis for the binding of *Escherichia coli* ribonuclease HI to RNA-DNA hybrids using surface plasmon resonance" J Biol Chem. Aug. 29, 1997;272(35):22015-22).*
International Search Report, dated Jul. 22, 2004.
European Supplemental Search Report for PCT/US0341097, dated Aug. 9, 2007.
Berk et al., Sizing and Mapping of Early Adenovirus mRNAs by Gel Electrophoresis of S1 Endonuclease-Digested Hybrids, *Cell.*, vol. 112, 721-732 (Nov. 1977).
Wang et al., "Hydroxyl Radical "footprinting" of RNA: Application to Pre-mRNA Splicing Complexes", *Proc. Natl. Acad. Sci. USA*, vol. 86, 7795-7799 (Oct. 1989).
Kashiwagi et al., "Proposal for New Catalytic Roles for Two Invariant Residues in *Escherichia coli* Ribonuclease HI", *Protein Eng.*, vol. 9:10, pp. 857-867 (1996).

* cited by examiner

*Primary Examiner*—Kenneth R. Horlick
*Assistant Examiner*—Christopher M. Babic
(74) *Attorney, Agent, or Firm*—Husch Blackwell Sanders Welsh & Katz

(57) ABSTRACT

Methods for specific RNA capture, detection and quantification are presented utilizing a protein that selectively binds RNA:DNA hybrids, preferably an RNase H that is modified to reduce degradation of the nucleic acid molecules and enhance specific detection of mixed RNA:DNA nucleic acid hybrids. Labeling of the RNA and/or amplification is not required to perform these methods. Modified RNase H enzymes useful in such methods are disclosed.

24 Claims, 9 Drawing Sheets

Fig. 4

```
SEQ ID NO:1    MLKQVEIFTD  GSCLGNPGPG  GYGAILRYRG
SEQ ID NO:2    MLKQVEIFTD  GSCLGNPGPG  GYGAILRYRG
SEQ ID NO:3    MLKQVEIFTD  GSCLGNPGPG  GYGAILRYRG
SEQ ID NO:4    MTKQVEIFTD  GSCLGNPGPG  GYGAILRYRG
SEQ ID NO:5    MTKQVEIFTD  GSCLGNPGPG  GYGAILRYRG

SEQ ID NO:1    REKTFSAGYT  RTTNNRMELM  AAIVALEALK
SEQ ID NO:2    REKTFSAGYT  RTTNNRMELM  AAIVALEALK
SEQ ID NO:3    REKTFSAGYT  RTTNNRMELM  AAIVALEALK
SEQ ID NO:4    REKTFSAGYT  RTTNNRMELM  AAIVALEALT
SEQ ID NO:5    REKTFSAGYT  RTTNNRMELM  AAIVALEALT

SEQ ID NO:1    EHCEVILSTD  SQYVRQGITQ  WIHNWKKRGW
SEQ ID NO:2    EHCEVILSTD  SQYVRQGITQ  WIHNWKKRGW
SEQ ID NO:3    EHCEVILSTD  SQYVRQGITQ  WIHNWKKRGW
SEQ ID NO:4    EHCEVILSTD  SQYVRQGITQ  WIHNWKKRGW
SEQ ID NO:5    EHCEVILSTD  SQYVRQGITQ  WIHNWKKRGW

SEQ ID NO:1    KTADKKPVKN  VDLWQRLDAA  LGQHQIKWEW
SEQ ID NO:2    KTADKKPVKN  VDLWQRLDAA  LGQHQIKWEW
SEQ ID NO:3    KTAGKKPVKN  VDLWQRLDAA  LGQHQIKWEW
SEQ ID NO:4    KTAEKKPVKN  VDLWQRLDLA  IQSHTIQWEW
SEQ ID NO:5    KTAGKKPVKN  VDLWQRLDLA  IQSHTIQWEW

SEQ ID NO:1    VKGHAGHPEN  ERCDELARAA  AMNPTLEDTG
SEQ ID NO:2    VKGHAGHPEN  ERCAELARAA  AMNPTLEDTG
SEQ ID NO:3    VKGHAGHPEN  ERCAELARAA  AMNPTLEDTG
SEQ ID NO:4    VKGHAGHPEN  ERCAELARQG  ANSPTLDDVG
SEQ ID NO:5    VKGHAGHPEN  ERCAELARQG  ANSPTLDDVG

SEQ ID NO:1    YQVEV
SEQ ID NO:2    YQVEV
SEQ ID NO:3    YQVEV
SEQ ID NO:4    YLPES
SEQ ID NO:5    YLPES
```

Fig. 7
A
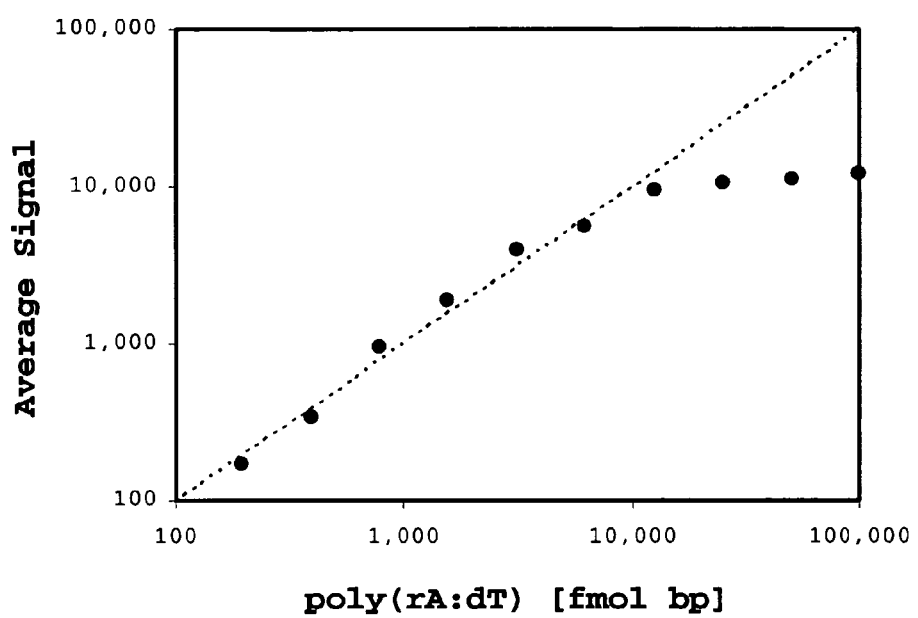
B

METHODS OF CAPTURING, DETECTING AND QUANTIFYING RNA:DNA HYBRIDS AND A MODIFIED RNASE H USEFUL THEREIN

CROSS-REFERENCE TO RELATED APPLICATIONS

This application is a non-provisional patent application which claims the benefit of priority of U.S. Provisional Patent Application Ser. No. 60/435,136 filed Dec. 19, 2002. The disclosures of the prior provisional patent application and the prior art cited and discussed below are incorporated in full herein by reference.

BACKGROUND OF THE INVENTION

The present invention is in the field of nucleic acid detection methods, particularly the detection of RNA:DNA hybrids; and also in the field of proteins having RNA:DNA hybrid-binding activity.

Current detection methods of RNA:DNA hybrids include immunodetection methods using monoclonal antibodies. In one such immunodetection method, monoclonal antibodies are raised to a RNA:DNA heteropolymer duplex prepared by transcription of a single-stranded DNA with DNA-dependent RNA polymerase. A monoclonal antibody with the highest affinity and specificity is selected. The antibody and an alkaline phosphatase-labeled second antibody are used to measure (via calorimetric response) hybrids formed between immobilized DNA probes of varying lengths and 23S ribosomal DNA. See, Boguslawski et al., "Characterization of Monoclonal Antibody to DNA:RNA and Its Application to Immunodetection of Hybrids," *J. Immunol Methods*, 1986 May 1; 89(1): 123-30.

Several proteins bind to RNA:DNA hybrids, notably including RNA polymerases, which typically polymerize RNA from DNA templates, but also include reverse transcriptases, which typically polymerize DNA based upon RNA templates. Ribonuclease H(RNase H) biochemical activity also includes the binding of RNA:DNA hybrids. Several reverse transcriptases and polymerases have RNase H biochemical activity, including the exonuclease aspect of the activity.

RNases H are a ubiquitous enzyme family that is divided into two distinct phylogenetic sub-types, Type 1 and Type 2. The RNases H are unified by the common ability to bind a single-stranded (ss) RNA that is hybridized to a complementary DNA single strand, and then degrade the RNA portion of the RNA:DNA hybrid. While the RNases H have been implicated in DNA replication and recombination, and repair, their physiological roles are not completely understood. In vitro, the enzymes will also bind double-stranded (ds) DNA, ssDNA, ssRNA, and dsRNA, albeit with lower affinities than they bind to RNA:DNA hybrids.

The present inventors found a way to exploit the ability of proteins that recognize and bind to RNA:DNA hybrids in order to provide a basis for novel methods to quantify specific RNA sequences in a mixed or pure population of RNA molecules. The present inventors also contemplate the use of proteins that recognize and bind RNA:DNA hybrids in other novel applications, such as the capture of whole families of RNAs all containing the same or closely-related nucleotide sequences.

Furthermore, the present inventors found a way to make the RNA:DNA hybrid binding protein, RNase H, more useful for the methods suggested in the preceding paragraph, by overcoming or minimizing the following problems of the RNase H enzymes of the art.

A wild-type RNase H has RNA-degrading activity, which can pose a problem for applications to the recognition of RNA:DNA hybrids such as those contemplated by the present inventors. For example, RNA-degradation may degrade the RNA to be specifically detected in RNA:DNA hybrids. For this reason, the RNA:DNA hybrid recognizing antibody methods of the art typically use enzymes, such as reverse transcriptase, that is lacking in this exonuclease aspect of RNase H activity. Further, a wild-type RNase H binds other types of nucleic acid in addition to RNA:DNA hybrids. In the methods of the present invention, it is preferable that binding of RNA:DNA hybrids is enhanced over other kinds of nucleic acid binding, such as single stranded nucleic acid. Accordingly, there is room for improvement of the discrimination between RNA:DNA hybrids over other kinds of duplex nucleic acid.

Due to the ubiquity of the enzyme, RNase H, there are several sequences for RNase H known in the literature. There are several RNase H enzymes known in the art, and their amino acid sequences vary widely. U.S. Pat. No. 5,268,289 discloses a thermostable RNase H, as does U.S. Pat. No. 5,500,370. U.S. Pat. No. 6,376,661 discloses a human RNase H and compositions and uses thereof. U.S. Pat. No. 6,001,652 discloses a human type 2 RNase H. U.S. Pat. No. 6,071,734 discloses RNase H from HBV polymerase.

The protein sequence database, NCBI (National Center for Biological Information), lists several references for submitted protein sequences that are identical to the *E. coli* RNase H of SEQ ID NO:1, e.g. gi24111645 and gi24050418 (matching all 155 of the 192 residues listed); gi15799890, gi15829464, gi16128201, gi133163, gi17311, gi443433, gi443227, gi1942322, gi42062, gi42777, gi147680, and more (matching 155 of 155 residues listed); gi1942213 discloses an alteration of residue 134 from aspartic acid (D) to anything; gi1942211 discloses the mutation from D (aspartic acid) to A (alanine). An early nucleotide sequence in the public database for RNase H1 has a point error that results in one too few cysteine residues in the protein.

In counterpoint to the present invention, the art teaches several RNA detection methods that utilize reverse transcriptase lacking RNase H biochemical activity. Examples include those methods disclosed in U.S. Pat. Nos. 6,277,579 and 5,994,079 "Direct Detection of RNA mediated by Reverse Transcriptase lacking RNAse H Function." U.S. Pat. Nos. 5,668,005 and 5,405,776 disclose genes for reverse transcriptase lacking RNase H activity.

In another area of the art, antisense nucleic acid methods, RNase H is utilized to cleave RNA. See Published U.S. Patent Application No. 20010044145, published Nov. 22, 2001, "Methods of using mammalian RNase H and compositions thereof," which teaches a method of promoting inhibition of expression of a selected protein by an antisense oligonucleotide targeted to an RNA encoding the selected protein, wherein RNase H binds to an oligonucleotide-RNA duplex and cleaves the RNA strand to promote inhibition of protein expression.

In summary, there is a need for an RNase H that has less RNA-degrading (nucleolytic) activity. There is a need for an RNase H with enhanced binding to RNA:DNA hybrids. There is a great demand for improved discrimination between RNA:DNA hybrids and other forms of nucleic acid, such as ssDNA, ssRNA, dsDNA and dsRNA.

BRIEF SUMMARY OF THE INVENTION

The present invention provides novel RNA:DNA hybrid detection methods that utilize the ability of RNA:DNA hybrid binding proteins to recognize and bind to RNA:DNA hybrids. The RNA:DNA hybrid binding ability forms the basis of a method to quantify specific RNAs (most probably mRNAs) in a mixed population of messages, as well as other applications such as the capture of whole families of RNAs that all contain the same or closely-related nucleotide sequences.

Most of the methods of the present invention, including methods of specific RNA detection, involve the detection of the presence or absence of an RNA:DNA hybrid. A possible RNA:DNA hybrid is exposed to an RNA:DNA hybrid binding protein under conditions such that the RNA:DNA hybrid binding protein would bind to the RNA:DNA hybrid if it were present. If the RNA:DNA hybrid binding protein is bound, then an RNA:DNA hybrid is present. The determination of the RNA:DNA hybrid can be qualitative or quantitative.

In some embodiments of the present invention, the possible RNA:DNA hybrid is formed between a DNA probe designed to hybridize to a target RNA and an analyte that may contain the target RNA. Such embodiments include the detection of specific RNA sequences or families of RNA in a test solution, which may also include a heterogeneous mixture of RNA and DNA. In some embodiments, either the DNA probe or the RNA:DNA hybrid binding protein are immobilized on a solid support. In some embodiments, the methods are sensitive enough that the solid support can be a chip with small amounts of material fixed upon it. In other embodiments, reaction wells are contemplated. In still other embodiments, a homogenous "one-pot" detection method is contemplated, with no solid phase.

The RNA:DNA hybrid binding protein is a polymerase, nuclease, reverse transcriptase, or a combination of a nuclease and polymerase. A contemplated RNA:DNA hybrid binding protein is other than an antibody. In preferred embodiments, the RNA:DNA hybrid binding activity is favored over other biochemical activities, including binding other forms of nucleic acid or nucleolytic or polymerizing activities. The biochemical activity is modified either through alteration of the biological sequences of the proteins, or through manipulation of the reaction conditions.

Thus, the invention contemplates a method for the detection of specific RNA sequences. In a specific RNA sequence detection method, an RNA-containing solution is hybridized to a DNA probe that is complementary to the RNA sequence of interest. An RNA:DNA hybrid binding protein, other than an antibody, is added to the RNA mixture with the DNA probe. The bound protein is detected.

The invention also contemplates a method for the quantitative analysis of specific RNA sequences. In a quantitative RNA detection method, an RNA-containing solution is hybridized to a DNA probe that is complementary to the specific target RNA. An RNA:DNA hybrid binding protein that preferentially binds to RNA:DNA hybrid molecules is added to the test solution. The amount of specific RNA present is quantified through measurement of the amount of bound protein.

In the specific RNA detection methods, the RNA:DNA hybrid binding protein is a nuclease and/or polymerase. In some preferred embodiments, the nuclease and/or polymerase is used under conditions where the protein exhibits RNA:DNA hybrid binding activity, but substantially reduced nucleolytic or polymerase activity. In some preferred embodiments, the RNA:DNA hybrid binding protein is a derivative of a nuclease and/or polymerase that is modified such that it does not exhibit the nuclease or the polymerase activities, or both, while still maintaining RNA:DNA hybrid binding activity.

In some preferred embodiments, the protein is a derivative of a nuclease and/or polymerase that is modified to decrease either the nuclease or polymerase activity (or both), and is further modified to improve its selectivity and/or affinity of binding RNA:DNA hybrids.

In some preferred embodiments, the protein is a member of the RNase H family of proteins used under conditions where it exhibits substantially reduced nuclease activity. In some preferred embodiments, the protein is a derivative of a member of the RNase H family of enzymes modified such that it does not exhibit nuclease activity and further modified to improve its selectivity and/or affinity for RNA:DNA hybrids. In some preferred embodiments, the RNase H has a biological sequence that is homologous to that of the E. coli RNase H1.

In some preferred embodiments using a DNA probe, the DNA probe is immobilized, preferably on a solid surface. In some preferred embodiments using an immobilized DNA probe or an immobilized RNA:DNA hybrid binding protein, the detection or quantification is accomplished via surface plasmon resonance or surface plasmon resonance imaging and related techniques.

In some preferred embodiments, detection or quantification is accomplished via a readily-assayable molecule fused to the protein that preferentially binds to RNA:DNA hybrid molecules. In some preferred embodiments, detection or quantification is accomplished via a specific antibody to the protein that preferentially recognizes RNA:DNA hybrid complexes.

In some preferred embodiments, the method of detection and/or quantification of RNA is accomplished in a homogeneous assay. In a homogeneous assay, the RNA population is hybridized to a DNA probe complementary to the RNA sequence of interest. The protein that preferentially binds to RNA:DNA hybrid duplexes is added to the mixture under conditions where it binds to RNA:DNA hybrids but does not degrade RNA. In this embodiment, the protein is added pre-bound to nucleic acid in such a way as to quench a fluorescent molecule incorporated into the protein:nucleic acid complex. The RNA:DNA hybrid binding protein is permitted to dissociate from the complex and re-associate with RNA:DNA hybrids from the RNA population. The newly-bound protein is detected and/or quantified by fluorescence measurement.

In some preferred embodiments, the detection or quantitation of specific RNA sequences is accomplished using proteins that exhibit RNase H activity. In such a method, the RNA population is hybridized to an immobilized DNA probe complementary to the RNA sequence of interest. Unhybridized nucleic acid is digested using single-strand specific exonucleases. The digested material and exonucleases are removed by washing. At least one protein that demonstrates RNase H activity is added and permitted to degrade hybrids between the RNA population and the DNA probe, liberating mono- and oligoribonucleotides. A single-strand specific RNA exonuclease is added to digest any liberated RNA oligonucleotides down to monomers. A system to generate ATP from any liberated AMP is added. The ATP thus produced is then used to drive an easily-assayable ATP detection reaction.

In some preferred embodiments of RNA detection, the protein that preferentially hybridizes to RNA:DNA hybrid duplexes is used to isolate specific RNA molecules or families of RNA molecules from a heterogeneous population. In such a method, the RNA population is hybridized to a DNA probe complementary to the RNA sequence of interest. The protein is added under conditions where it can bind to RNA:DNA hybrids. Then the bound RNA molecules are recovered. In a preferred embodiment of the preceding RNA detection method, the protein is immobilized and the bound RNA:DNA eluted after washing to remove unbound nucleic acid. Preferably, recovery of the protein/RNA:DNA complex is accomplished by digesting unbound RNA and DNA with exonucleases, removing unbound protein (e.g. by passing the mixture over immobilized RNA:DNA hybrids), and recovering protein-RNA:DNA complex using affinity purification.

In some embodiments, the methods of the invention are applied to the detection of single base mismatches in RNA. Single-stranded DNA oligonucleotides (at least about 8 nucleotides in length, preferably not more than 50 nucleotides long, more preferably not more than 10 nucleotides long) are provided that are totally complementary to the RNA sequence of interest. Also provided are single-stranded DNA oligonucleotides (similar length) that are complementary to the RNA sequence of interest except for a specific single base alteration that the RNA of interest may carry. Either of those DNA oligonucleotides are hybridized to the solution containing the RNA of interest whose sequence is to be determined. The RNA:DNA hybrid binding protein is added to the mixture, and binding detected and/or quantified for each of the oligonucleotides. Greater binding to the RNA:DNA hybrid, in the reaction using the oligodeoxynucleotide containing the single base alterations, indicates the presence of the altered sequence.

Also contemplated are protection assays, wherein the RNA:DNA hybrid binding protein, preferably RNase H, is permitted to bind to RNA hybridized to DNA probes. Footprinting digestion (e.g. hydroxyl radical bombardment) is used to assay the binding of the RNA:DNA hybrid binding protein to the hybrids.

For the modified RNase H derivatives described herein, the DNA sequences encoding proteins having those amino acid sequences are also contemplated, preferably using the preferred codon usage for the species, which are well-known in the art for many species, including *E. coli*.

The present invention further provides a modified RNase H enzyme that has enhanced binding affinity and selectivity for RNA:DNA hybrids and/or decreased nucleolytic activity.

The present invention has many benefits and advantages, several of which are listed below.

One benefit of the specific RNA detection method is that it is useful for the detection of one or more specific RNAs in a mixture of RNA molecules.

One advantage of the RNA detection method is that it is useful for detecting mRNAs that are only expressed at relatively low levels by labeling either RNA or the DNA probe.

A benefit of using a modified RNase H in the disclosed methods is that the sensitivity and selectivity of the assays are enhanced relative to the use of a typical native RNase H.

An advantage of some embodiments of the invention is that methods using the modified RNase H permit precise and straightforward quantitation of specific sample RNAs without the need for either chemical or enzymatic conversion of the sample RNA to an intermediate form, which can introduce bias into the measurements.

These benefits and more will be evident to a person of skill in the art from this disclosure.

BRIEF DESCRIPTION OF THE DRAWINGS

In the drawings forming a portion of this disclosure,

FIG. 4 shows a comparison between various RNase H sequences. SEQ ID NO:1 is the wild type *Escherichia coli* RNase H1 enzyme, that has all of the usual RNase H biochemical activities described herein. SEQ ID NO:2 has a single D to A mutation at position 134, which decreases nucleolytic activity >1000 fold while increasing RNA:DNA hybrid affinity ~2-fold relative to the wild type. SEQ ID NO:3 has the D134A and also a D→G at position 94. SEQ ID NOs:4 and 5 have mutations at 134 and 94, and also share A→L109, L→I111, G→Q112, Q→S113, Q→T115, K→Q117, A→Q139, A→G140, M→N142, N→S143, E→D147, T→V149, Q→L152, V→P153 and V→S155. Additionally, SEQ ID NO:5 has a G at position 94, as did SEQ ID NO:3, whereas SEQ ID NO:4 has an E at position 94. The novel sequences (SEQ ID NO:3, 4 and 5) all display an increase in RNA:DNA binding affinity and binding selectivity for RNA: DNA relative to other nucleic acids.

FIG. 7 illustrates the feasibility of direct RNase H-mediated detection of RNA:DNA hybrids on a solid support. To eliminate ambiguities of hybridization efficiency, known quantities of poly rA:dT, an RNA:DNA homopolymer, were spotted directly onto a charged nylon membrane. RNase H labeled with a single radionucleotide was added, allowed to bind, and excess washed away. The resulting autoradiograph of the nylon membrane is shown in FIG. 7 section B and graphic representation of the data is shown in FIG. 7 section A. The average radioactive signal corresponding to bound RNase H, increases in direct proportion to the amount of RNA:DNA hybrid in the spot. These data also demonstrate the sensitivity of RNA:DNA hybrid detection, easily down through the picomolar nucleic acid range.

FIG. 8 shows the actual membranes and the mRNA expression at 37 degrees Celsius and at 50 degrees Celsius, and the control with no mRNA.

DETAILED DESCRIPTION OF THE INVENTION

Figure 1:
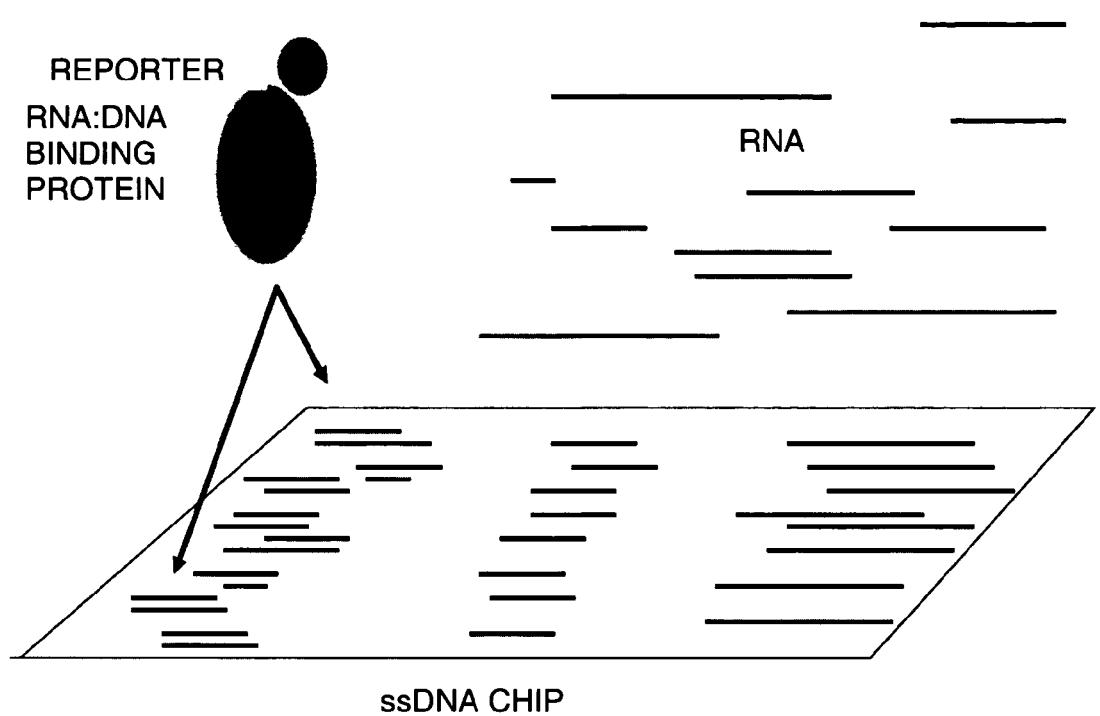
FIG. 1 illustrates an embodiment for the detection and quantitation of a specific RNA (most probably mRNA) on a DNA chip, as discussed hereinbelow and also illustrated in Example 1. The DNA chip has on it ssDNA oligonucleotides of defined sequence immobilized at defined locations. Contacting the chip with a preparation of mRNA permits duplex formation (hybridization) to occur between the RNA and complementary DNA molecules on the chip. Unbound RNA is washed away. A protein that binds to RNA:DNA hybrid, such as a modified RNase H, is linked to a suitable reporter or label. The labeled RNA:DNA binding protein is introduced and permitted to bind the RNA:DNA hybrid molecules on the chip. Unbound material is then washed off and the remaining material assayed. This RNA detection method provides a quantitative readout of how much of each of the various pre-selected specific RNA species was present in the original heterogeneous population.

The present invention provides technological applications of RNA:DNA heteroduplex-binding proteins. RNase H1, and some RNase H enzymes are preferred for use in methods of the invention. The methods of the invention exploit the ability of a protein to selectively recognize and bind to RNA:DNA hybrids in order to provide a basis for novel methods to quantify specific RNAs in a mixed or pure population of RNA molecules. The invention also contemplates the use of RNA:DNA binding proteins in other novel applications, such as the capture of whole families of RNAs all containing the same or closely-related nucleotide sequences.

Most of the methods of the present invention, including methods of specific RNA detection, share the following steps for the detection of the presence or absence of an RNA:DNA hybrid. A possible RNA:DNA hybrid is provided. The possible RNA:DNA hybrid is exposed to an RNA:DNA hybrid binding protein for a time period and under conditions such that the RNA:DNA hybrid binding protein would bind to the RNA:DNA hybrid if it were present. Then it is determined whether the RNA:DNA hybrid binding protein is bound. If the RNA:DNA hybrid binding protein is bound, then an RNA:DNA hybrid is present.

In the sections that follow, various embodiments of the contemplated RNA detection methods are discussed, in addition to some RNase H proteins useful with the contemplated methods.

In one set of RNA detection embodiments, the present invention provides a method for the detection of specific RNA sequences in a homogeneous or heterogeneous population of RNA molecules using proteins that naturally exhibit RNA:DNA hybrid binding activity, preferably RNase H that has been modified to eliminate nucleolytic activity and to enhance binding to RNA:DNA hybrids and/or to improve selectivity for RNA:DNA hybrids. The RNA detection method includes the steps that follow. The RNA population is hybridized to a DNA probe that is complementary to the RNA sequence of interest. The RNase H derivative is added to the mixture under conditions such that it can bind any RNA:DNA hybrids. The bound RNase H is detected and/or quantified. Alternatively, RNase H is utilized under conditions under which the nucleolytic activity is substantially suppressed, such as minimal access to divalent cations (e.g. magnesium ions).

Specific RNA Detection

The present invention contemplates an embodiment for the detection and/or quantitation of specific RNA molecules, preferably mRNA molecules, using a DNA bound to a solid support, preferably a DNA chip.

Methods for specific RNA detection will have numerous applications in the art. In an example below, the methods of the present invention were used to analyze the expression of heat shock proteins under various conditions. Applications will include the determination of disease states, progression of development, among a great many others that are evident to workers in the art.

For this embodiment, a single-stranded DNA probe is provided, preferably that has a known nucleotide sequence. The DNA probe should be of sufficient length for hybridization, therefore at least 8 nucleotides in length. Preferably the DNA probe is from 8 to about 100 nucleotides in length, most preferably from 10 to about 50 nucleotides in length, with 10 to 30 nucleotides being most particularly preferred for a the length of the DNA probe.

In order to realize maximum sensitivity in the present invention without having to label the RNA, the DNA probe may be labeled, for example radioactively, fluorescently or chemically. The DNA probe may contain nucleotides that are non-standard, in other words, not the typical A, G, C, or T nucleotides. The DNA probe may contain nonstandard linkages, such as degradation-resistant phosphorothioate linkages in place of the typical phosphate linkages.

In a preferred embodiment, the DNA probe is attached to a solid support. Examples of such solid supports for DNA are well known in the art, and include glass plates (such as those used in a DNA probe array on a DNA chip) and nylon membranes. DNA chip references include U.S. Pat. No. 6,368,808 "DNA chip and its Preparation" and U.S. Pat. No. 6,342,359 "Method for Detecting Nucleic Acids, Detector for Nucleic Acids, and Method for Producing the Same". In an embodiment where multiple DNA probes are to be challenged with an RNA-containing sample, it is preferred that known DNA sequences are present in defined regions on the solid support, so that the sequence of the DNA probe at any position can be determined by the person analyzing the assay results, if they so choose.

For this embodiment, an RNase H enzyme is provided, preferably a modified RNase H that has reduced RNA degradation activity and/or preferably a modified RNase H that has an enhanced RNA:DNA hybrid binding selectivity.

In a preferred embodiment, the RNase H enzyme is linked to a suitable reporter system. Reporter systems are known in the art, and many are usable with the present invention. Examples of such reporter systems include luciferase/luciferin, alkaline phosphatase, and direct fluorescent labeling of the RNase H protein. The luciferase/luciferin reporter system generates luminescence when ATP is present as a substrate. The alkaline phosphatase reporter system generates light when the appropriate substrate is present, such as fluorescence when used in conjunction with the AttoPhos™ AP Fluorescent Substrate System (Promega Corporation).

A sample that may contain RNA for which the presence or absence is being determined may be from any source. For example, a mixed sample of RNA from a total RNA isolation from cells may provide a source to be analyzed, such as the RNA obtained using RNAgents™ (total RNA isolation system, from Promega Corporation) or PolyATtract™ (mRNA isolation system, Promega Corporation). In a preferred embodiment, the RNA is an mRNA sample comprising a mixture of mRNA molecules. When RNase H or another protein that selectively binds RNA:DNA hybrids over other nucleic acid types is used, the need to pre-treat the sample to isolate mRNA away from other types of nucleic acid is lessened, but still preferred for the most sensitive assays.

Contacting the DNA probe with the RNA sample under conditions that permit hybridization will allow duplex RNA:DNA hybridization between the DNA probe and a sufficiently complementary RNA. When the DNA is bound to a solid support, the non-hybridized portion of the RNA sample is preferably washed away, leaving an RNA:DNA hybrid formed bound to the solid support. In a preferred embodiment, a DNA chip is exposed to an mRNA sample, permitting the mRNA to bind to the DNA chip wherever complementary sequences permit. Then the chip is washed and assayed for binding using the RNase H method according to the present invention.

The solid support is analyzed to determine the presence of RNA:DNA hybrid through the use of RNase H, preferably the modified RNase H described herein. In a preferred embodiment, the RNase H is labeled, as described above. RNase H is introduced and permitted to bind the RNA:DNA hybrid molecules on the solid support. Unbound material is then washed off and the remaining material assayed.

In some embodiments, this mRNA detection method provides a quantitative readout of how much of a particular mRNA species was present in the original heterogeneous population.

An alternative contemplated detection method uses Surface Plasmon Resonance Imaging (SPIR). See, Nelson, BP et al., Surface Plasmon Resonance Imaging Measurements of DNA and RNA Hybridization Adsorption Onto DNA Microarrays, *Anal. Chem.* 73(1):1-7 (Jan. 1, 2001). SPIR eliminates the need for a reporter molecule or labeling of the RNA:DNA hybrid binding protein.

In order to improve the sensitivity of the SPIR detection method, an antibody specific for RNase H can be bound to the surface containing the complex of RNase H and the bound RNA:DNA hybrid. Further improvement to the sensitivity can be achieved using the specific antibody for RNase H bound to solid nanoparticles such as gold.

Homogeneous Specific RNA Assay

Figure 2:
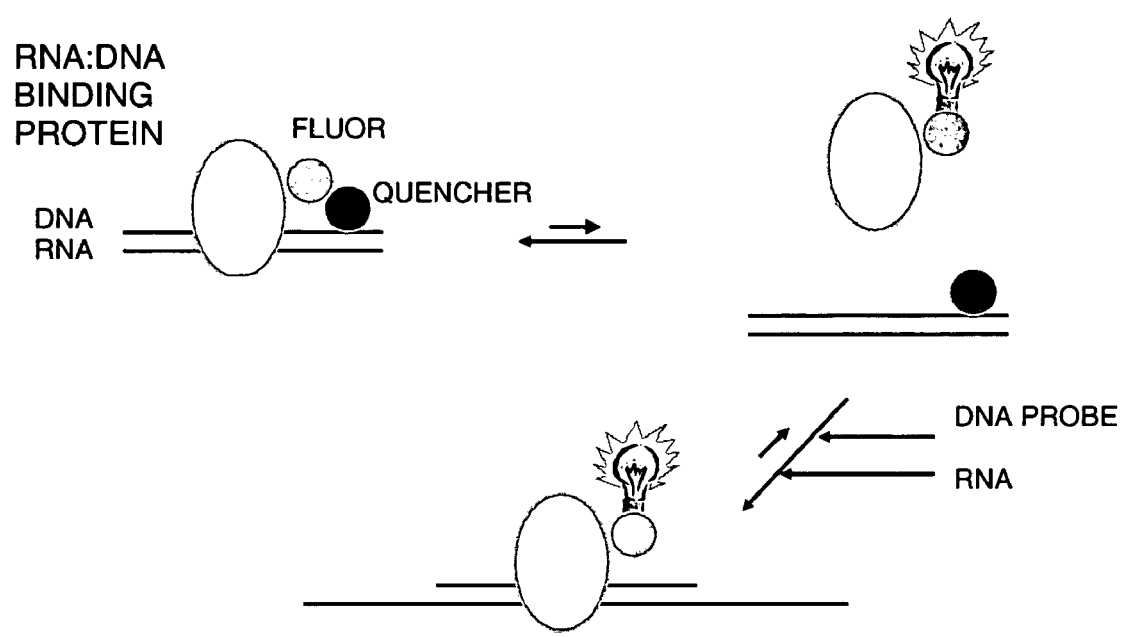
FIG. 2 illustrates an embodiment of detection and quantification of RNA (most probably mRNA) in a homogeneous assay as described hereinbelow and demonstrated in Example 2. An RNA:DNA binding protein, for example a modified RNase H, is bound to a duplex nucleic acid molecule (RNA:RNA or DNA:DNA) in such a manner that a fluorescent tag on the RNA:DNA binding protein is masked by a quencher molecule attached to the nucleic acid, or vice versa. In the absence of other targets for the RNA:DNA hybrid binding protein, the fluorescence is largely quenched. In the presence of a specific target mRNA hybridized to a suitable probe DNA, the RNA:DNA hybrid binding protein now has additional, non-quenching targets to which to bind, permitting fluorescence. In this manner, the amount of a specific RNA species is measured (quantitatively or qualitatively) in a single-tube (homogeneous) assay.

The present invention contemplates the detection of a specific RNA (most probably mRNA) in a homogeneous assay, with optional quantitative data. An embodiment of this aspect of the invention is illustrated in FIG. 2. In a preferred embodiment, dual-component signal is used, such as fluorescence quenching, to monitor the binding to RNase H of the desired RNA complexed with probe DNA in an RNA:DNA hybrid.

An RNase H bound to a duplex nucleic acid molecule in such a manner that a quencher molecule attached to the nucleic acid masks the fluorescent tag on the RNase H. It is also contemplated that the quencher molecule be attached to the RNase H and the nucleic acid be attached to the fluorescent molecule. Fluor/quencher molecule pairs are well-known in the art, as are the methods of modifying protein and nucleic acid with molecules that fluoresce and/or quench.

In this embodiment, it is preferred to use a modified RNase H. In the absence of targets for the RNase H other than the nucleic acid with the quencher molecule, bound protein is in equilibrium with unbound material, with the equilibrium favoring the bound molecules, and the fluorescence is largely quenched. This is the starting point for the assay to detect a specific RNA. Preferably, the nucleic acid molecule bound to the RNase H, prior to the challenge with the sample RNA to be assayed, is chosen such that the following is true under the assay conditions: RNase H binds it more avidly than either of the individual nucleic acid components (the RNA sample or ssDNA probe), and RNase H binds it less avidly than the target RNA:DNA hybrid complex (formed from the RNA to be assayed with a ssDNA probe).

An excess of RNA extract, which may contain the desired specific RNA, is added to the (preferably modified) RNase H, together with a suitable DNA probe capable of hybridizing to the specific, target RNA. When the specific target RNA is duplexed with the probe DNA, the RNase H has additional, non-quenching targets to which to bind, and the RNase H binding equilibrium shifts away from the quenching material, permitting more fluorescence to be detected. This method permits the specific RNA species to be measured (quantitatively or qualitatively) in a single-tube (homogeneous) assay.

RNA:DNA Hybrid Binding Proteins

The use of RNA:DNA hybrid binding proteins is contemplated in the RNA:DNA hybrid detection methods of the present invention. There are several classes of enzymes that bind to RNA:DNA hybrids. These include polymerases, reverse transcriptases and nucleases. Antibodies that may specifically bind RNA:DNA hybrids are not contemplated for the present invention.

Examples of contemplated RNA:DNA hybrid binding proteins that are polymerases include RNA polymerase. In addition, several reverse transcriptase enzymes, typically associated with RNA viruses such as HIV, which generate DNA from an RNA genome, have a polymerase domain and an RNase H domain. After a first strand of DNA is made that is complementary to the RNA, the RNase H domain removes the RNA so that a second DNA strand can be synthesized in its place. A polypeptide having essentially only RNA:DNA binding without RNA synthetic or degradative activities is preferred in several embodiments of the present invention.

The polymerase and nuclease activities of enzymes that bind to RNA:DNA hybrids can be minimized through omission of the metal ion cofactors required for effective polymerase/nuclease biochemical activity, such as magnesium ions. Thus, without modification of the protein sequence, but only through control of the RNA:DNA hybrid binding conditions, the biochemical activity of an RNA:DNA hybrid binding protein can be altered in a manner that is preferred in several embodiments of the present invention. For example, it is contemplated that the RNase H activity of reverse transcriptase is made more useful in a process of the present invention by scrupulously avoiding the presence of magnesium ions. Without magnesium ions, the nucleolytic activity of reverse transcriptase is significantly diminished.

The biochemical activity of the polymerase or nuclease can be modified through modification of the amino acid sequence. For example, certain residues known in the art to be required for the polymerase activity but not the RNA:DNA hybrid binding can be altered.

Types of contemplated modifications that are beneficial for some embodiments of the invention include linkage of the RNA:DNA hybrid binding protein to a tag to facilitate purification. Such modifications are well-known in the protein purification arts and are contemplated for the preparation of RNA:DNA hybrid binding protein for use with the present invention, but are not considered by the present inventors to be central to the invention. As a well-known example, some protein purification columns take advantage of the tight binding of biotin and streptavidin. The appropriate modification is made in the protein to adhere it specifically to a column for fast purification. Another well-known example is the fusion of a histidine stretch for specific binding to a column.

Another type of contemplated modification that is beneficial for some embodiments of the invention includes linkage of the RNA:DNA hybrid binding protein to a reporter molecule (e.g. fluorescent tag) to facilitate detection of the RNA:DNA hybrid binding protein.

RNase H and Modified RNase H

RNase H enzymes are contemplated for use as an RNA:DNA hybrid binding protein in several embodiments of the invention. In some preferred embodiments of the present invention, the biochemical activities of RNase H are modified.

In some embodiments, a contemplated modified RNase H has decreased nucleolytic activity. In several embodiments of the present invention for detection of RNA, nuclease activity can degrade nucleic acids to be detected in the RNA:DNA hybrid. As discussed in the general case with polymerases and nucleases that exhibit RNA:DNA hybrid binding activity, above, modification of the conditions, such as omission of magnesium ions, will decrease nuclease activity of RNase H. As discussed below, modification of the amino acid sequence can also decrease nucleolytic activity. Some embodiments are contemplated wherein the nucleolytic activity modification is combined with a modification of the nucleic acid binding activity.

Native RNase H binds other types of nucleic acid in addition to RNA:DNA hybrids with varying affinities (RNA:DNA>>ssDNA and ssRNA>dsDNA>dsRNA). For many applications, it is preferable when binding of RNA:DNA hybrids over other kinds of nucleic acids is enhanced. Accordingly, there is room for improvement of RNase H's ability to discriminate between RNA:DNA hybrids and other kinds of nucleic acids.

The methods of the present invention may be carried out with proteins having known RNase H activities. RNase H activity includes binding to a single-stranded (ss) RNA that is hybridized to a complementary DNA single strand, and cleaving the RNA portion of the RNA:DNA hybrid. In vivo, RNase H plays roles in DNA replication and recombination, and may also have other functions. In vitro RNase H is known to bind double-stranded (ds) DNA, single-stranded (ss) DNA, ssRNA, and dsRNA, albeit with much lower affinity than it binds to the mixed RNA:DNA nucleic acid hybrids.

The present methods of the invention of using RNase H are useful with any RNase H, not merely those polypeptides having exactly SEQ ID NO:1 through SEQ ID NO:5. The minimal requirement is that the RNase H have RNA:DNA hybrid binding activity. Thus, for example, thermostable (see, e.g. U.S. Pat. Nos. 5,268,289 and 5,500,370) and human RNase H enzymes (see, e.g. U.S. Pat. No. 6,376,661) that have different biological sequences from SEQ ID NO:1 through SEQ ID NO:5 are contemplated for use in the methods of the invention, and also for the reagents or kits or products for carrying out the methods of the invention.

In some preferred embodiments, a modified RNase H enzyme as described herein, or variants thereof, is used. "Variants" of amino acid sequences include internal additions, internal deletions, conservative and non-conservative amino acid exchanges and code for a polypeptide which has the RNA:DNA hybrid binding activity of RNase H. Substitutions of a naturally-occurring amino acid residue with a non-naturally-occurring analog, particularly as a marker, are also specifically contemplated. Fusions at either terminus of other polypeptides, residues, markers, purification tags or enzyme domains are also contemplated.

For use in methods and compositions of the present invention, two types of biochemical activity modifications were combined in the most preferred RNase H (SEQ ID NO:5). These are (i) elimination of the DNA-degrading (nucleolytic) activity and (ii) enhancement of binding to RNA:DNA hybrids. The improvement in binding combines both an increase in affinity and discrimination for RNA:DNA hybrid binding relative to binding to other forms of nucleic acid (ssDNA, ssRNA, dsDNA or dsRNA).

Specifically contemplated for a modified RNase H enzyme is that, when optimally aligned to SEQ ID NO:1 through SEQ ID NO:5, as shown in the attached Biological Sequence Listing, and also in FIG. 4 herein, (i) the amino acid residue corresponding to position 134 is an alanine residue (A or Ala), (ii) the residue corresponding to position 94 is preferably a glycine residue (G or Gly), less preferably an aspartic acid (D or Asp) or glutamic acid (E or Glu) residue, and (iii) at least two, preferably five, most preferably all, of the residues are as listed below:

| Corresponding Residue Position | Amino Acid Residue |
|---|---|
| 2 | T (Thr) |
| 60 | T (Thr) |
| 109 | L (Leu) |
| 111 | I (Ile) |
| 112 | Q (Gln) |
| 113 | S (Ser) |
| 115 | T (Thr) |
| 117 | Q (Gln) |
| 139 | Q (Gln) |
| 140 | G (Gly) |
| 142 | N (Asn) |
| 143 | S (Ser) |
| 147 | D (Asp) |
| 149 | V (Val) |
| 152 | L (Leu) |
| 153 | P (Pro) |
| 155 | S (Ser) | where in some preferred embodiments, the sequence has at least 4 of the 6 changes from residues 109 to 117, inclusive; in some preferred embodiments, the sequence has at least 5 of the 9 changes from residues 139 to 155.

The expression "conservative amino acid exchange" relates to an exchange of an amino acid residue for another amino acid residue, where the exchange does not lead to a change in polarity or charge, and preferably to little or no change in size where there is no change in polarity or charge. An example of a conservative amino acid exchange is the exchange of a non-polar amino acid residue for another non-polar amino acid residue.

The homology of polypeptide molecules that are related to one another can be determined with the aid of known methods. As a rule, special computer programs with algorithms are employed that take account of the particular requirements. Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (Wis.)); BLASTP, BLASTN and FASTA (Altschul, S. et al., J. Molec. Biol 215:403/410 (1990)). The BLAST X program can be obtained from the National Centre for Biotechnology Information (NCBI) and from other sources (BLAST Handbook, Altschul S., et al., NCB NLM NIH Bethesda Md. 20894; Altschul, S., et al., J. Mol. 215:403/410 (1990)). The known Smith Waterman algorithm can also be used for determining homology. Nucleic acids useful in preparing a disclosed RNase H enzyme are also contemplated. Such nucleic acid sequences (genomic DNA, cDNA, synthetic DNA, constructs and RNA), upon expression and translation, provide a polypeptide sequence that has the functional properties enumerated herein. A worker of ordinary skill in the art, through routine procedures and known methods and codon usage, is able to derive a useful nucleic acid sequence given the amino acid sequences disclosed herein. Cloning and recombinant expression in a suitable host cell are accomplished using the methods and materials known in the art.

Constructs are contemplated that comprise nucleic acid sequences that encode a disclosed RNase H protein. A construct preferably is suitable for expression and includes a promoter for controlling expression of the contemplated nucleic acid. The choice of promoter is a routine matter of selection, and typically depends upon the expression system used for expression. Constitutive or inducible promoters (e.g. metallothionein), are typical. Vectors including regulatory regions are also typical, for example, bacteriophages, lambda derivatives, adenoviruses, vaccinia viruses, baculoviruses, SV40 viruses and retroviruses. Numerious prokaryotic and eukaryotic expression systems are known in the art. Typical host cells include prokaryotic cells, e.g E. coli or B. Subtilis, and eukaryotic cells, e.g, yeast, plant, insect cells, and mamammalian cells (e.g. CHO, COS, and HeLa cells). Also contemplated are transgenic plants or plant cell cultures expressing the desired protein. The materials and methods for such expression are known in the art, and it is a matter of routine procedure to select and adapt a system for expression of the desired RNase H protein.

Also contemplated are nucleic acid sequences whose exon sequence will provide a contemplated polypeptide. The term "exon sequence" refers either to a eukaryotic gene sequence interrupted by an intron sequence or to the corresponding sequence in the RNA transcript. The exon sequence(s) and the non-coding intron sequences are transcribed together; the intron transcript or transcripts are then deleted to obtain the functional RNA.

Examples of DNA sequences are provided in the accompanying Biological Sequence Listing, the disclosures of which are incorporated herein by reference. DNA sequences modified for expression and translation in E. coli that encode polypeptides having amino acid sequences SEQ ID NO:4 and SEQ ID NO:5 are provided as SEQ ID NO:6 and SEQ ID NO:7. Also contemplated are the counterstrand nucleic acids (DNA and RNA), and nucleic acid sequences that, on the basis of the genetic code, are degenerate to the sequences SEQ ID NO:6 and 7.

Further contemplated are RNase H fusion proteins that contain the disclosed functional RNase H enzymes or derivative enzymes. Typical examples are fusions with a marker, purification or linker polypeptide that is helpful for providing a protein or assay exploiting the RNase H RNA:DNA hybrid binding activity.

It is a matter of routine procedure to adapt procedures known in the art for preparing proteins to develop a process for the preparation of a disclosed RNase H protein. Preferably, a nucleic acid molecule or construct encoding the disclosed RNase H protein is expressed in a suitable host cell and the protein is isolated from the host cell or the medium through the use of conventional processes.

EXAMPLE 1

Specific mRNA Detection

This Example of the invention is illustrated in FIG. 1, in an embodiment for the detection and quantitation of specific mRNAs on a DNA chip.

A DNA chip is provided that has immobilized on it ssDNA oligonucleotides of defined sequence at known locations. The DNA chip is contacted with a test sample preparation of mRNA, which has a heterogeneous mRNA population, in order to permit duplex formation (hybridization) to occur between the RNA and complementary DNA molecules on the chip. Unbound mRNA is washed away.

A modified RNase H linked to luciferase is provided. The modified RNase H is introduced and permitted to bind the RNA:DNA hybrid molecules on the DNA chip. Unbound material is then washed off and the remaining material assayed using a luciferin/ATP system. The light output is read on a luminometer to determine the amount of RNase H bound to each of the defined regions of the DNA chip. An increased intensity of light output occurs where there is a larger amount of labeled, modified RNase H bound to an RNA:DNA hybrid. If there is no RNA:DNA hybrid, then RNase H should not be bound at the site; therefore, the light output from the luciferase/luciferin reaction is minimal.

The light output is compared to a standard curve of known amounts of labeled, modified RNase H to provide quantitative data regarding the amount of a RNA:DNA hybrid, and thus how much of a hybridizing mRNA species is present in the RNA sample.

EXAMPLE 2

Homogeneous mRNA Assay

This example demonstrates the detection and/or quantitation of mRNA in a homogeneous assay. A modified RNase H that has enhanced RNA:DNA hybrid binding properties relative to a native RNase H and reduced nucleic acid degrading properties is provided. The modified RNase H is bound to a duplex nucleic acid molecule in such a manner that quencher molecule attached to the bound nucleic acid masks a fluorescent tag on the RNase H. In the absence of targets for the RNase H other than the nucleic acid with the quencher molecule, bound protein is in equilibrium with unbound material, and the equilibrium favors the bound molecules, so the fluorescence is largely quenched. This is the starting point for the assay to detect a specific mRNA.

An excess of mRNA extract that may contain the desired specific mRNA is added to the quenched modified RNase H, together with a suitable DNA probe capable of hybridizing to target specific mRNA message. If the specific target mRNA is duplexed with the probe DNA, the RNase H now has additional, non-quenching targets to which to bind, and the RNase H binding equilibrium shifts away from the quenching material and permits more RNase H to fluoresce. In this manner, the amount of a specific RNA species is measured (quantitatively or qualitatively) in a single-tube (homogeneous) assay.

EXAMPLE 3

Detection of RNA Message Families

For application to families of RNA, the DNA probe preferably has complementary base pair homology throughout the length of the probe binding to the RNA family, such that the variation in the RNA family is outside of the region of homology.

Figure 3:
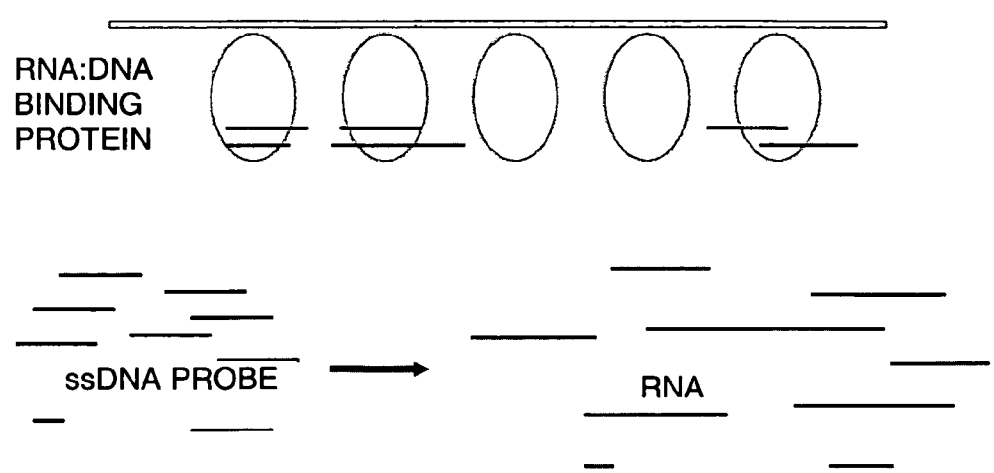
FIG. 3 illustrates an RNA detection method utilizing specific RNA capture described in Example 3. Immobilized RNA:DNA hybrid binding protein provides a specific RNA capture system to separate specific messages or message families from a heterogeneous mRNA pool. The specific RNA messages or message families bind to the DNA probe and the RNA:DNA hybrid binding protein binds to the RNA:DNA hybrid.

This example demonstrates an RNA detection method utilizing specific RNA capture described in FIG. 3. An RNase H molecule that is modified to enhance its RNA:DNA hybrid binding ability is immobilized on a solid surface. An mRNA sample is mixed with one or more DNA probes and permitted to form RNA:DNA hybrids. The DNA probes are labeled. The solution containing the RNA:DNA hybrids is then contacted with the RNase H bound to the solid support. The RNA:DNA hybrids bind to the RNase H and are thereby retained on the solid support while the unbound portion of the analyte is washed away.

Immobilized RNase H provides a specific RNA capture system to separate specific messages or message families from a heterogeneous mRNA pool. The specific RNA messages or message families bind to the DNA probe and the modified RNase H binds to the RNA:DNA hybrid.

EXAMPLE 4

Modified RNase H

This example compares the biochemical activity of a variety of RNase H enzymes having different amino acid sequences, to highlight the important regions for activity-affecting sequence alterations and contemplated variations of the recited amino acid sequences.

In addition to wild-type RNase H, a mutation of the RNase H sequence has been known in the art for several years which decreases RNA nucleolytic activity >1000 fold while increasing RNA:DNA hybrid affinity ~2-fold relative to the wild type (published data). FIG. 4 shows an alignment of the wild type RNase H enzyme sequence (SEQ ID NO:1) with this nuclease deficient isolate (SEQ ID NO:2). The protein with SEQ ID NO:2 served as the substrate for the mutation and iterative selection for enhanced RNA:DNA binding affinity and selectivity. Two independent mutagenesis protocols were used to generate the two pools of mutant RNases H. In one set, the gene coding for SEQ ID NO:2 was subject to random point mutagenesis. In the second protocol, the gene coding for SEQ ID NO:2 [E. coli rnh1(D134A)] was subject to random in vitro recombination with two other homologous RNase H1 genes, Yersinia pestis rnh1(D134A), Klebsiella pneumoniae rnh1(D134A) to create chimeric RNaseH1 genes.

The two pools were independently subjected to a competitive, iterative selection process to enrich for isolates with improved hybrid binding characteristics. Biochemical characterization of the proteins that were preferentially selected identified a "best" protein from each pool (characterization discussed below). The sequences of the "best" candidate from each are shown, SEQ ID NO:3 and SEQ ID NO:4. Both SEQ ID NO:3 and SEQ ID NO:4 retained the original D134A point mutation of SEQ ID NO:2 and were found to have enhanced RNA:DNA hybrid affinity and selectivity to ssDNA, ssRNA, DNA:DNA and RNA:RNA hybrid binding activities.

The present inventors were able to combine the attributes of both "best" RNase H isolates into a single "best of the best" protein (SEQ ID NO:5). By introducing the single glycine point change from position 94 of SEQ ID NO:3 into the same position within a protein of SEQ ID NO:4, they created a modified RNase H enzyme of the present invention.

Protein expression constructs were made for the individually selected and combined mutants and transferred into E. coli using standard procedures well-known in the art. The proteins were purified and then characterized in parallel to the nuclease-deficient D134A mutant of wild type RNase H that served as the parent molecule in the selections.

Figure 5:
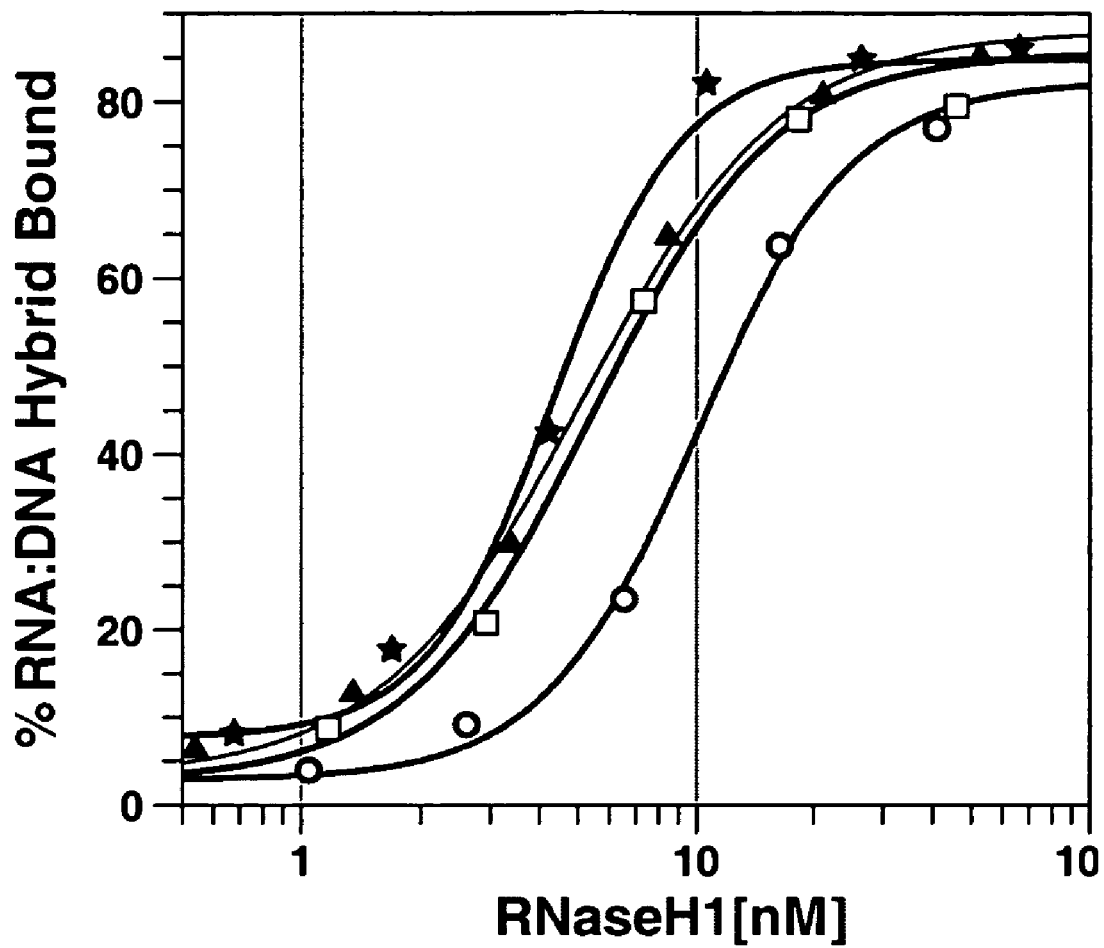
FIG. 5 shows an RNA:DNA binding affinity curve for the RNase H enzymes described in FIG. 4. The RNase H with the highest RNA:DNA hybrid affinity is SEQ ID NO:5, denoted by the binding curve with the solid stars. The open squares mark the RNA:DNA hybrid binding curve of SEQ ID NO:4. The solid triangles mark the RNA:DNA hybrid binding curve of SEQ ID NO:3. The open circles mark the RNA:DNA hybrid binding curve of SEQ ID NO:2. The wild type SEQ ID NO:1 is not shown, but has a lower binding affinity than SEQ ID NO:2 (as noted in the caption to FIG. 5) and a correspondingly lower affinity than SEQ ID NOs:3, 4 and 5.

FIG. 5 shows the observed increase in RNA:DNA binding affinity for the various RNase H enzymes as assayed in a nitrocellulose filter binding experiment, a procedure well-known in the art for quantitative determination of protein: nucleic acid affinities. In the experiment, serial dilutions of the indicated RNase H proteins were individually incubated in 1×FB Buffer [100 µg/ml BSA; 50 mM NaCl; 1 mM EDTA; 20 mM HEPES, pH 7.0] with a radiolabeled RNA:DNA hybrid of the following sequence:

RNA:DNA#1

SEQ ID NO: 6  5'-GGACCGGAAAGGUACGAGCAUGUGA-3'  (RNA)

SEQ ID NO: 7  3'-CCTGGCCTTTCCATGCTCGTACACT-5'  (DNA)

(The DNA strand of hybrid RNA:DNA#1 was singly end-labeled with the radionuclide $^{32}$P for the experiment.)

After 30 minutes incubation at 25° C., the 50 µl reactions were filtered quickly through buffer-equilibrated nitrocellulose filters and washed twice with 500 µl Wash Buffer [10% Glycerol, 50 mM NaCl; 1 mM EDTA; 20 mM HEPES, pH 7.0]. Proteins bind to nitrocellulose while double stranded nucleic acids do not; therefore, the radioactivity on the filter directly reflects the protein-bound nucleic acids. The amount of RNA:DNA hybrid retained by each filter was directly quantitated from the damp filters by Cerenkov counting. Each protein was tested in triplicate and the results averaged. Control filters to determine total input radioactivity were used to calculate the percent of total input hybrid bound. SDS-PAGE and densitometry re-confirmed protein concentrations.

The RNA:DNA hybrid in the reactions is present at a pM concentration, well below the $K_D$ of the interaction. Accordingly, the protein concentration required for half-maximal saturation equals the binding constant. Using this fact, the data presented in FIG. 5 (and tabulated in the following section) demonstrate both the absolute and relative affinity of each protein for this RNA:DNA hybrid. The data indicate that the selected mutant proteins, SEQ ID NOs:3 and 4 represented by the filled triangle and open squares respectively, display a higher affinity for this RNA:DNA hybrid relative to the parent SEQ ID NO:2, open circles. Similar data originally identified the best candidate proteins, referred to herein as SEQ ID Nos:3 and 4, from the pool of selected candidates. In addition, the "combined" mutant, SEQ ID NO:5 (filled stars) binds RNA:DNA hybrids with slightly greater affinity than either of the "component" proteins.

Figure 6:
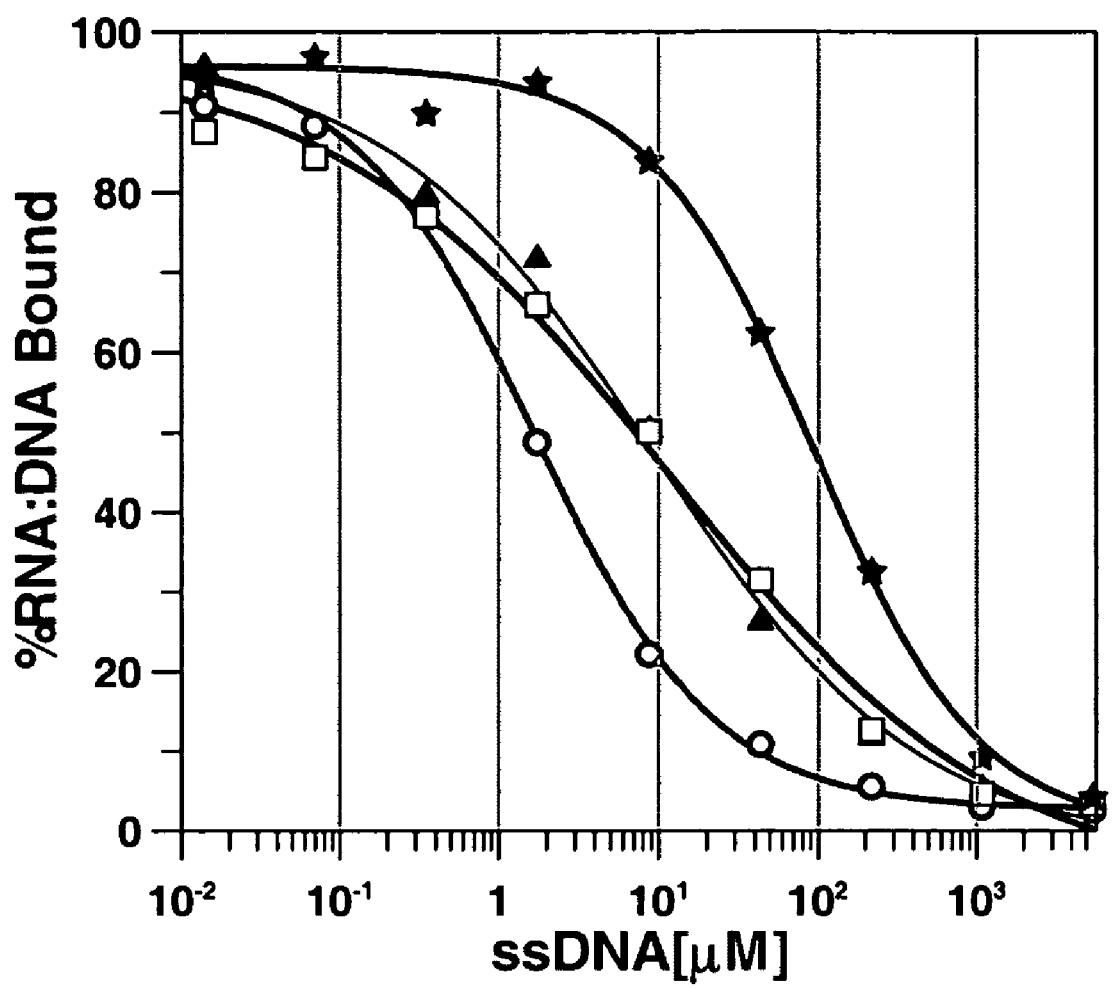
FIG. 6 shows an equilibrium competition assay. It is important to note that a pico-molar amount of RNA:DNA hybrid was mixed with the micromolar amounts of ssDNA indicated prior to addition of the mutant RNase H proteins. Accordingly, the experiment directly displays the improved abilities of the claimed RNase H proteins (SEQ ID NOs:3, 4, and 5) to selectively recognize and bind an RNA:DNA hybrid in the presence of a large excess of ssDNA competitor. The RNase H with the lowest ssDNA affinity or the greatest ability to resist competition by ssDNA is SEQ ID NO:5, denoted by the binding curve with the solid stars. The open squares mark the ssDNA competition curve of SEQ ID NO:4. The solid triangles mark the ssDNA binding curve of SEQ ID NO:3. The open circles mark the ssDNA binding curve of SEQ ID NO:2. The wild type SEQ ID NO:1, not shown, displays a ssDNA binding affinity equivalent to SEQ ID NO:2.

FIG. 6 demonstrates the ability of the different RNase H proteins to selectively locate and bind to an RNA:DNA hybrid in the presence of a vast excess of competitor nucleic acids as tested in an equilibrium competition experiment, a standard variation of the nitrocellulose filter binding experiment described in the previous paragraphs. In the experiment, labeled RNA:DNA hybrid was mixed with serial dilutions of single-stranded DNA, freshly heat-denatured sheared salmon sperm DNA. Prior experimentation identified the conditions for maximal sensitivity. Competitions with either ssDNA, dsDNA, or ssRNA demonstrated that ssDNA is the most effective nucleic-acid competitor for RNA:DNA hybrid binding to RNase H. RNase H was added to a final concentration equivalent to its RNA:DNA affinity, which results in binding of ~40% of the input RNA:DNA hybrid (½ maximal saturation as determined above). Each ssDNA concentration was tested in duplicate. After 30 min incubation at 25° C., the reactions were processed, radioactivity quantitated and samples averaged as indicated above.

Under the condition of half maximal saturation, the reactions are maximally sensitive to inhibition by competitor molecules. Control reactions without added competitor nucleic acids were used both to judge that the condition of half maximal saturation was met for each protein/hybrid combination and to normalize the final data to 100% in the final analysis.

The results of this example are represented graphically in FIG. 6 and tabulated below ($IC_{50}$ for ssDNA). The $IC_{50}$ equals the $K_D$ of the RNases H for ssDNA or, inversely, reflects the affinity of the RNase H mutants for ssDNA. The data indicate that each of the individually selected mutants, SEQ ID NOs:3 and 4 (represented by filled triangles and open squares respectively), has a decreased affinity for ssDNA. Combining the mutations, as in SEQ ID NO:5, results in a further increase in RNA:DNA hybrid selectivity (data represented by filled stars).

To confirm that the observed increase in RNA:DNA hybrid sequence selectivity was a general phenomenon and not an artifact of the specific nucleic acid sequences analyzed, two additional RNA:DNA hybrids, of different sequence than RNA:DNA#1, were compared in parallel filter binding and equilibrium competition demonstrations as detailed above. The sequences of the original and the alternative RNA:DNA hybrids are shown.

```
                        RNA:DNA#1
SEQ ID NO: 6  5'-GGACCGGAAAGGUACGAGCAUGUGA-3' (RNA)
SEQ ID NO: 7  3'-CCTGGCCTTTCCATGCTCGTACACT-5' (DNA)

RNA:DNA#2
SEQ ID NO: 8  5'-GGCGAACAGGACUGCGUAUGAUAGG-3' (RNA)
SEQ ID NO: 9  3'-CCGCTTGTCCTGACGCATACTATCC-5' (DNA)

RNA:DNA#3
SEQ ID NO: 10 5'-AGUUCGACGAGCAUGGAGAGGUCAG-3' (RNA)
SEQ ID NO: 11 3'-TCAAGCTGCTCGTACCTCTCCAGTC-5' (DNA)
```

The results of these additional experiments produced similar results to those depicted in FIG. 5 and FIG. 6.

The critical values from all twenty-four independent titration curves are tabulated below. As detailed in the preceding paragraphs, the $K_D$ for RNA:DNA hybrids was derived from nitrocellulose filter binding data and reported as nM RNase H, the final concentration of RNase H in reactions that achieve half-maximal binding of the indicated RNA:DNA hybrid. The $IC_{50}$ for ssDNA, generated from equilibrium competition assays, is reported as μM ssDNA present in the complete reaction.

| Protein Hybrid | SEQ ID NO: 2 | | SEQ ID NO: 3 | |
| --- | --- | --- | --- | --- |
| | $IC_{50}$ (μM ssDNA) | $K_D$ (nM Hybrid) | $IC_{50}$ (μM ssDNA) | $K_D$ (nM Hybrid) |
| RNA:DNA#1 | 1.7 ± 0.2 | 10.0 ± 0.4 | 9 ± 3 | 5.1 ± 0.4 |
| RNA:DNA#2 | 5.5 ± 0.4 | 8.0 ± 0.6 | 15 ± 4 | 6.0 ± 0.5 |
| RNA:DNA#3 | 2.9 ± 0.2 | 8.0 ± 0.2 | 10 ± 2 | 5.5 ± 0.3 |

| Protein Hybrid | SEQ ID NO: 4 | | SEQ ID NO: 5 | |
| --- | --- | --- | --- | --- |
| | $IC_{50}$ (μM ssDNA) | $K_D$ (nM Hybrid) | $IC_{50}$ (μM ssDNA) | $K_D$ (nM Hybrid) |
| RNA:DNA#1 | 12 ± 4 | 5.0 ± 0.3 | 94 ± 6 | 4.3 ± 0.4 |
| RNA:DNA#2 | 55 ± 4 | 7.7 ± 0.2 | 84 ± 6 | 1.8 ± 0.1 |
| RNA:DNA#3 | 33 ± 3 | 7.1 ± 0.3 | 44 ± 5 | 1.7 ± 0.3 |

For all three RNA:DNA hybrid sequences tested, the relative trends of RNA:DNA and ssDNA affinity are maintained regardless of the input hybrid's sequence. The RNases H of SEQ ID NO:3 and SEQ ID NO:4 had primarily higher RNA:DNA hybrid binding selectivity over ssDNA than the RNase H of SEQ ID NO:2. The RNase H having SEQ ID NO:5 exhibits both a higher affinity for RNA:DNA hybrids and a lower degree of competition by ssDNA than SEQ ID NOs:2, 3, or 4. The observed improvement in RNase H's RNA:DNA hybrid binding character, independent of the RNA and DNA sequences of the RNA:DNA hybrid, demonstrates that the enhanced selectivity of RNA:DNA hybrid binding is a general phenomenon and not sequence-dependent for the mutations described herein.

In order to quantitate the degree of RNase H improvement, we chose to define "hybrid selectivity" for each individual RNase H by dividing the affinity for ssDNA ($IC_{50}$) by the RNA:DNA dissociation constant ($K_D$). The values for each hybrid sequence were then normalized relative to the "hybrid selectivity" calculated for the protein of SEQ ID NO:2. The normalized values for the RNases H of SEQ ID NOs:2, 3, 4, and 5 are tabulated below:

| Hybrid Selectivity | SEQ ID NO: 2 | SEQ ID NO: 3 | SEQ ID NO: 4 | SEQ ID NO: 5 |
| --- | --- | --- | --- | --- |
| RNA:DNA#1 | 1 | 10 | 14 | 129 |
| RNA:DNA#3 | 1 | 4 | 10 | 68 |
| RNA:DNA#4 | 1 | 5 | 13 | 72 |
| Average | 1 | 6 | 12 | 90 |

The RNase H proteins of SEQ ID NO:3 and SEQ ID NO:4 exhibit enhancements of 6- and 12-fold respectively in RNA:DNA hybrid selectivity. The RNA:DNA binding character of the RNase H protein having SEQ ID NO:5 is enhanced by almost two orders of magnitude, by far the best of the group disclosed herein.

This data also demonstrate that SEQ ID NO:3 and SEQ ID NO:4 embody autonomous mechanisms of enhanced selectivity. If the mechanisms are distinct, a 6-fold and a 12-fold increase should combine to create an approximately 72-fold improvement in selectivity. The independent experimental determination of a ~90-fold increase in selectivity for SEQ ID NO:5 confirms that the combination of the independent amino acid changes of SEQ ID NO:3 and 4 achieve separate mechanisms of enhanced selectivity. The fact that the additive property is observed individually for all hybrids tested reconfirms that the mechanisms are likely to be general for the RNA:DNA-hybrid helical structure.

This Example demonstrates that preferred RNase H sequences of the present invention have a mutation that corresponds to a G in position 94 of SEQ ID NO:1 through SEQ ID NO:5 or an A in a position that corresponds to position 134 of SEQ ID NO:1 through SEQ ID NO:5. Particularly preferred RNase H sequence has G94 or A134 and at least one of the following mutations (relative to SEQ ID NO:1) A→L109, L→I111, G→Q112, Q→S113, Q→T115, K→Q117, A→Q139, A→G140, M→N142, N→S143, E→D147, T→V 149, Q→L152, V→P153 and V→S155. RNase H proteins having the preferred sequences exhibit increased discrimination in binding RNA:DNA hybrids over ssDNA and improved RNA:DNA hybrid binding affinity.

EXAMPLE 5

RNase H-Mediated Detection of RNA:DNA Hybrids on a Solid Support

The feasibility of RNase H-mediated detection of RNA:DNA hybrids on a solid support, depicted in FIG. 1, is illustrated in FIG. 7, A and B. Interpretation of the data requires an explanation of the methods employed.

The example required independent preparation of the detection system, a radioactively labeled RNase H, and the substrate, RNA:DNA hybrids tethered to a charged nylon membrane. The preparation and use of each is detailed in the following paragraphs.

To adapt RNase H for detection, the following DNA sequence was inserted at the 5' end of the RNase H (SEQ ID NO:5) gene:

Kinase (PKA) phosphorylation to the N-terminus of RNase H SEQ ID NO:5. Co-expression with BirA in *E. coli* in biotin-supplemented (50 μM) media produces an RNase H that is singly biotinylated (>95%) at the indicated lysine. Additionally, the purified protein can be phosphorylated in vitro by Protein Kinase A in the presence of [γ$^{33}$P]ATP. These post-translational modifications facilitate detection of the RNase H either directly through the radioactive label introduced by PKA or indirectly with a labeled avidin/streptavidin conjugate.

For this example, a biotinylated RNase H was labeled by PKA in the presence of [γ$^{33}$P]ATP. A standard 20 μl labeling reaction used 50 μM RNaseH1, 100 μM ATP, 100 μCi [γ$^{33}$P] ATP, and 10 U Protein Kinase A [1 U=1 nmol PO$_4$/min. transferred to KEMPTIDE™ (S6 kinase substrate having the sequence LRRASLG) at 30° C.]in 1×PKA Buffer [10 mM MgCl$_2$; 50 mM Tris-HCl, pH 7.5]. After 4 hours at 30° C., the reaction is essentially complete (>90% phosphorylated as assessed by TCA precipitation) and further labeling quenched by addition of 30 μl Stop Mix [0.84 mM EDTA; 1.7 mg/ml BSA]. Unreacted [γ$^{33}$P]ATP and buffer salts were removed by passage through two successive gel filtration spin columns (10 kDa exclusion) equilibrated with 1×HBS [150 mM NaCl; 1 mM EDTA; 0.01% Tween-20; 10 mM HEPES, pH 7.0 (DEPC Treated)]. Column purified $^{33}$P-RNase H was mixed with an equal volume of 100% glycerol for stabilization and storage. For each of the following experiments, the rigorous removal of residual $^{33}$P-ATP decreases non-specific background and ensures that detected radioactivity directly reflects the amount of bound RNase H.

In order to eliminate ambiguities of hybridization efficiency in the final analysis, the substrate membrane was prepared with pre-formed RNA:DNA hybrids. Homopolymer nucleic acids poly(rA) and poly(dT) were quantitated by UV absorbance. Equimolar amounts were mixed, heat denatured, and annealed in 1×HBS buffer. Serial dilutions of the poly (rA:dT) hybrids were spotted directly onto a GeneScreen Plus charged nylon membrane. The membranes were wetted in 2×SSC [0.3 M NaCl; 0.03 M Na$_3$Citrate; pH 7.0]. The nucleic acids were crosslinked to the damp membrane by 12 μJ UV irradiation. To decrease non-specific adsorption of RNase H to the membrane, the membranes were blocked with 1% Casein in 1×TBS [150 mM NaCl, 25 mM Tris-HCl, pH 7.20] for 1 hr. The selection of charged membranes and Casein as a blocker were determined to be the best pairing for RNase H mediated detection.

In the experiment, a solution containing 50 nM $^{33}$P-labeled RNase H (SEQ ID NO:5); 1 mg/ml BSA; 65 mM NaCl; 1 mM

```
5'ATGGCTGGCGGTCTGAACGATATTTTCGAAGCTCAGAAGATTGAATGGCAT

...M  A  G  G  L  N  D  I  F  E  A  Q  K  I  E  W  H
                             BIOTIN-TAG    *

AGCCGTAAAGGTAGCGGTGGCAAGCGGGGCTCTGGTCATATG-3'

S  R  K  G  S  G  G  K  R  G  S  G  H  M

PKA Motif *      PKA Motif *   Initial Met
                                    of SEQ ID NO: 5
```

Expression of this modified RNase H gene in *E. coli* fuses the peptide motifs for post-translational modification by biotin ligase (BirA) biotinylation and cAmp-dependent Protein EDTA; 20 mM HEPES, pH 7.0 was added and incubated 1 hr. at room temperature. Unbound RNase H was washed away by three washes with 1×TBST [150 mM NaCl, 0.05% Tween- 20; 25 mM Tris-HCl, pH 7.2] of 5, 5, and 15 min. respectively. The washed membrane was exposed to a storage phosphor and the average radioactive signal from each spot was quantitated using a Molecular Dynamics Storm840 phosphorimager. Exposure time was adjusted to keep the entire range of signals within the linear range of the phosphorimager.

The resulting phosphor-image of the nylon membrane after $^{33}$P-RNase H detection is shown in FIG. 7 section B and the graphic representation of signal quantitation is shown in FIG. 7 section A. The data demonstrate that the $^{33}$P-RNase H permits a direct readout of the amount of RNA:DNA hybrid present; $^{33}$P-RNase H bound increases in direct proportion to the amount of spotted RNA:DNA hybrid. Data from the low end of the detection suggest a detection limit in the range of 1 to 2 fmol of a 100 bp RNA:DNA hybrid. The signal plateau at higher RNA:DNA levels is due to saturation of the nucleic acid spot with RNase H. The assay configuration places the plateau at values that exceed the maximum possible with commercially available nylon-based arrays to maximize the utility of the assay's linear range.

EXAMPLE 6 mRNA Analysis of Genomic Expression under Heat Shock Stress

As an Example of the beneficial applicability of the methods of the present invention, a comparison was carried out against published results. The parallel analysis of changes in genomic expression in *E. coli* as a result of heat shock disclosed by C. S. Richmond, J. D. Glasner, R. Mau, J. Hongfan and F. R. Blattner, "Genome-wide expression profiling in *Escherichia coli* K-12," *Nucl. Acids Res.*, 27:3821-3835 (1999).

In that work all 4290 annotated open-reading frames of *E. coli* MG1655 were analyzed by spotting gene-length PCR fragments specific for each ORF (i) on charged nylon membranes and subsequent hybridization with radioactive cDNA, and (ii) on glass microarrays with subsequent hybridization to fluorescent cDNA. From the published data of Richmond et al., three genes (hs1U, hs1V, and ibpB) that were strongly up-regulated by heat stress and seven genes (ptsN, ho1A, endA, tufA, dnaN, speB, trmD) who were not identified as heat-regulated genes were selected as controls for this Example. The heat-shock response is mediated primarily at the level of transcript synthesis and provides an ideal system for the evaluation of the invention.

In this Example, using the methods of the invention, the expression of the ten genes, 3 heat-shock and 7 housekeeping genes, were analyzed in parallel. A culture of *E. coli* MG1655 was grown, split into 2 sub-cultures and one sub-culture was subjected to heat shock (50° C.) in accordance with Richardson et al. while the second sub-culture remained under non-stress conditions (37° C.) Total RNA was isolated by hot acid-phenol extraction followed by standard ethanol and LiCl precipitations. Due to the highly selective nature of the RNase H reagent of the invention, no further treatment of the sample RNA was required. Eliminating this extra step, which involves extensive nuclease treatment and re-purification, avoids the 40%-50% loss of sample that routinely results from this more stringent protocol.

The miniarray of ten genes on a charged nylon membrane was prepared. For each gene, oligonucleotide pairs were selected to amplify an approximately 500 bp PCR product corresponding to the gene of interest. The PCR products were amplified from *E. coli* MG1655 genomic DNA, cloned into a standard plasmid vector, and sequenced to confirm their identity. The DNA plasmid clone for each gene fragment served as substrates for the large scale PCR amplification of the gene fragment for array construction. Following procedures detailed in Richardson et al., the purified dsDNA PCR products were alkali denatured by mixing ~0.06 µg/ml DNA with [1 M NaOH; 30 mM EDTA] at a ratio of 2:1 respectively. Spots of 1 µl alkali denatured PCR DNA were then manually spotted onto GeneScreen Plus charged nylon membranes. Once all ten PCR products had been spotted, membranes were incubated for 5 minutes in 2×SSC+0.25 M Tris-HCl, pH 7.5. Following the neutralization step, the DNA was crosslinked to the membrane by exposure to 12 µJ UV light. Prior to hybridization, membranes were incubated with 1×FPH [5×SSC (750 mM NaCl; 75 mM Na$_3$Citrate); 1% SDS, 0.1% Ficoll; 0.1% Polyvinyl-pyrrolidone; 0.1% BSA (Grade V), 50% Formamide] at 42° C. for 30 minutes and then buffer discarded. The RNA samples of interest, at ~0.4 µg/ml in 1×FPH, were denatured at 70° C. for 15 min., added to the membranes, and hybridized for 40 hours at 42° C. A control without added RNA was performed in parallel. The membranes were subject to stringency washes at room temperature, two times for 5 minutes with 2×SSC, 0.1% SDS, twice with 0.2×SSC, 0.1% SDS under the same conditions. A quick rinse in 2×SSC preceded a 30 minute ssRNA-specific RNase wash [2×SSC+10 U/ml RNase T1; 1 µg/ml RNase A] to remove unhybridized RNA. Membranes were rinsed [2×SSC, 0.1% SDS] to remove residual RNase and UV crosslinked as before. $^{33}$P-RNase H-mediated detection and signal quantitation were performed as described in the previous example.

Figure 8:
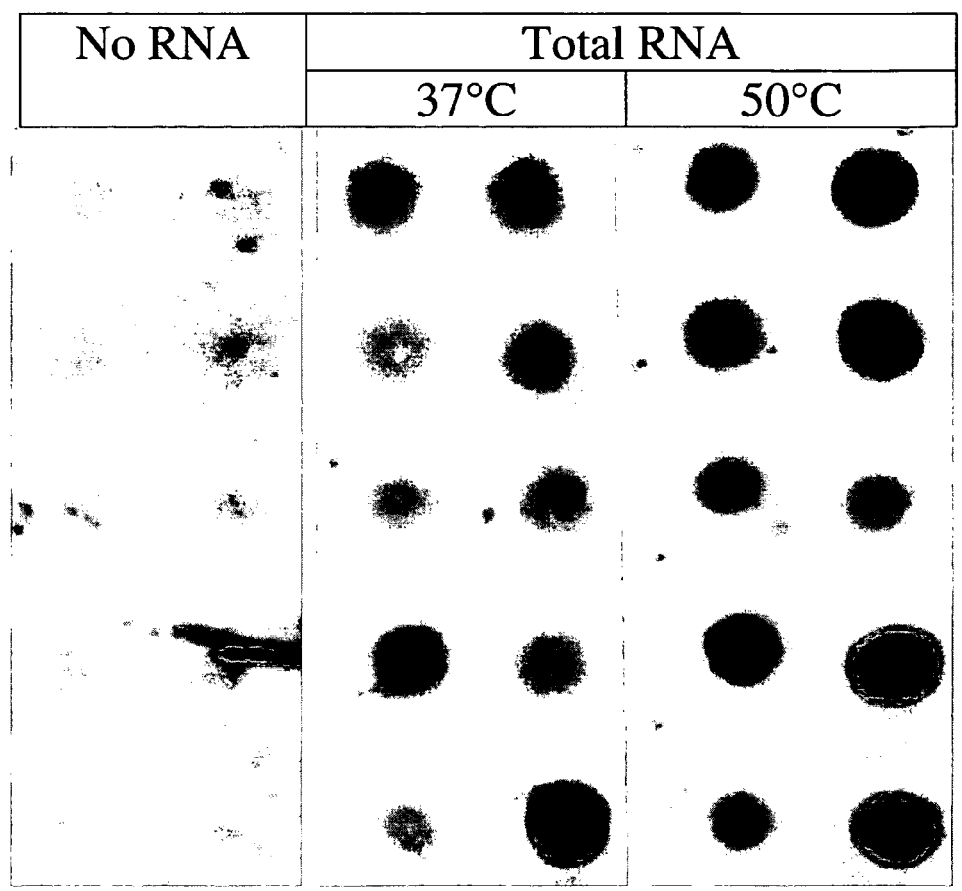
FIG. 8 illustrates the specific detection of mRNAs in an analysis of *E. coli* genomic expression changes in response to heat shock, as described in Example 6 hereinbelow.

The results of $^{33}$P-RNase H binding to the array are shown in FIG. 8. As before, the radioactive signal directly reflects the presence of bound RNase H. The left panel displays the control reaction without input RNA. The middle panel was derived from the 37° C. RNA sample and the right panel reflects the 50° C., heat-shocked, population. Each panel is oriented such that the identical genes are in identical positions within the array. The background signal for $^{33}$P-RNase H binding to the no RNA control membrane is slightly elevated relative to the two membranes exposed to RNA-containing buffers. The signal intensity of each spot reflects varied levels of expression of the genes studied. Even direct visual comparison of the raw data indicates that the relative spot intensities of at least three genes increase significantly upon heat shock.

Figure 9:
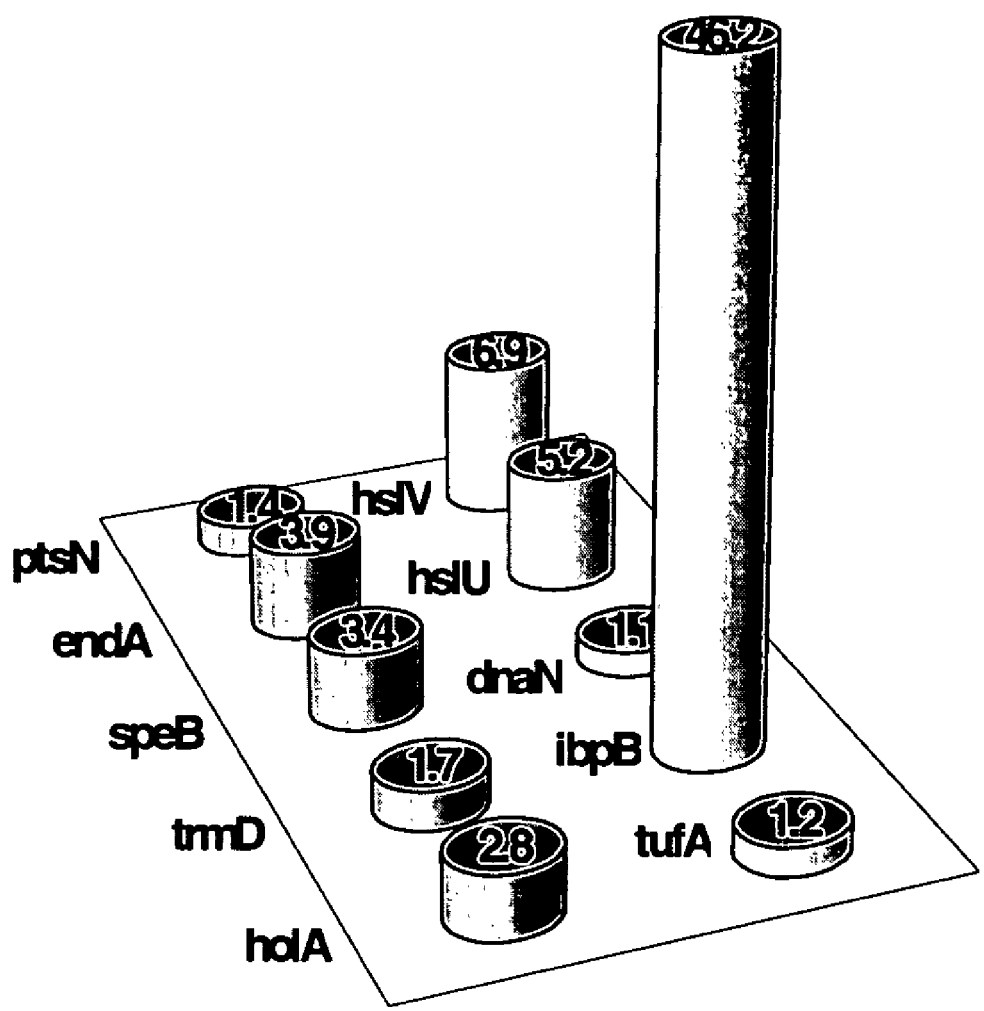
FIG. 9 is derived from the raw data shown in FIG. 8 and illustrates graphically the quantitative change in gene expression observed in response to heat shock for the ten genes discussed in Example 6.

The quantitative assessment is presented graphically in FIG. 9. The data presented were derived in the following manner: the average signal from each spot in the array determined, background signal from the no RNA control subtracted, and the ratio of signal from the 50° C. data set relative to the 37° C. data reported. Signal intensity from each spot reflects varied levels of expression of the genes studied. The observed changes in gene expression correlate with the published observations of Richardson et al. with some notable differences. Little change in expression was observed for the seven housekeeping genes. The data sets also agree in that ibpB is upregulated to a greater extent than either hslU or hslV. The absolute magnitude of the change in ibpB, estimated in this Example, is 46-fold as compared to values of 400 fold from Richardson et al. Similarly, the Example values for hslU and hslV are 5 and 7-fold relative to values of 16 and 32-fold respectively (Richardson et al.). Discrepancies between the methodologies' abilities to determine the absolute magnitude of regulation may reflect true differences in the methods or cumulative effects of slight differences in the growth phase and timing of the induced heat shock. One aspect should be method-independent; hslU and hslV are co-transcribed and should be equally represented in the population. With the expectation that hslU and hslV transcipt abundance is equimolar, the RNase H method gives values that are more nearly equimolar than the labelled cDNA method.

EXAMPLE 7

Specific mRNA Detection Using Reverse Transcriptase

This Example of the invention is analogous to Example 1 in that there are several DNA probes immobilized on a solid surface, such as a nylon membrane.

The DNA probes are contacted with a test sample preparation of mRNA, which has a heterogeneous mRNA population, in order to permit duplex formation (hybridization) to occur between the RNA and complementary DNA probes on the solid surface. Unbound mRNA is washed away.

A reverse transcriptase enzyme linked to a horseradish peroxidase domain is provided under magnesium-free conditions. The reverse transcriptase is introduced and permitted to bind the RNA:DNA hybrid molecules on the solid surface under magnesium-free conditions. Unbound material is then washed off and the remaining material assayed using a horseradish peroxidase visible light substrate system. The light output is read on a spectrometer to determine the amount of reverse transcriptase bound to each of the defined regions of the solid surface. An increased intensity of absorbance occurs where there is a larger amount of horseradish peroxidase-labeled, reverse transcriptase bound to an RNA:DNA hybrid. If there is no RNA:DNA hybrid, then reverse transcriptase should not be bound at the site and therefore the light absorbance from the products of the horseradish peroxidase reaction is minimal.

The absorbance is compared to a standard curve of known amounts of horseradish peroxidase-labeled reverse transcriptase to provide quantitative data regarding the amount of a RNA:DNA hybrid, and thus how much of a hybridizing mRNA species is present in the RNA sample.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. A method for the detection of a specific RNA sequence comprising the steps of:
   (a) providing a mixture that may contain an RNA:DNA hybrid molecule comprising a specific RNA sequence of interest and a DNA probe complementary to the RNA sequence;
   (b) combining the mixture with one or more modified *E. coli* RNase H having a sequence selected from the group consisting of SEQ ID NO. 3, 4, and 5 under conditions that permit binding of the modified *E. coli* RNase H to the RNA:DNA hybrid when such a hybrid is present to form a bound modified *E. coli* RNase H, and;
   (c) detecting the bound modified *E. coli* RNase H, wherein the binding indicates that an RNA:DNA hybrid molecule, and therefore a specific RNA sequence, is present.

2. The method according to claim 1 further comprising quantifying the specific RNA from measurement of the amount of bound modified *E. coli* RNase H detected in step (c).

3. The method according to claim 1 wherein the modified *E. coli* RNase H is used under conditions where it does not exhibit nuclease activity.

4. The method according to claim 1 wherein the DNA probe is immobilized on a solid support.

5. The method according to claim 4 wherein the detection step (c) or quantification is accomplished via surface plasmon resonance or surface plasmon resonance imaging.

6. The method according to claim 2 where the detection or the quantification is accomplished via a readily-assayed molecule fused to the modified *E. coil* RNase H.

7. The method according to claim 2 where the detection or quantification is accomplished via a specific antibody to the modified *E. coli* RNase H.

8. The method according to claim 1 where the modified *E. coli* RNase H is added in step (b) pre-bound as a complex with nucleic acid in such a way as to quench a fluorescent molecule incorporated into the modified *E. coli* RNase H/nucleic acid complex, allowing the modified *E. coli* RNase H to disassociate from the complex, permitting fluorescence, and re-associate with RNA:DNA hybrids from the mixture; and the detection of step (c) is carried out by measurement of fluorescence permitted by disassociation of the complex added in step (b).

9. The method according to claim 1 wherein the DNA probe is immobilized on a solid support wherein the detection of step (c) further comprises
   (1) digesting unhybridized nucleic acid using single-strand specific exonucleases;

(2) washing to remove digested material, exonucleases, and other unbound material;

(3) adding at least one protein that demonstrates RNase H activity;

(4) degrading bound RNA:DNA hybrid molecules to liberate mono- and oligoribonucleotides;

(5) adding a system to generate ATP from any AMP liberated from degraded RNA:DNA hybrid molecules and;

(6) employing an easily-assayable ATP detection reaction.

10. The method according to any one of claims 1-7 where step (c) comprises recovery of the bound modified *E. coli* RNase H.

11. The method of claim 10 where step (c) further comprises recovery of the specific RNA sequence where the bound RNA:DNA hybrid is eluted after washes.

12. The method according to claim 10 where recovery of the bound modified *E. coli* RNase H is accomplished in a process comprising:
  i. Digestion of unbound RNA and DNA with exonucleases;
  ii. Removal of unbound protein by passing the mixture over immobilized RNA/DNA hybrids; and
  iii. Recovery of bound modified *E. coli* RNase H by affinity purification.

13. The method according to claim 1 applied to the detection of single base mismatches in RNA,
  wherein the DNA probe in step a that is complementary to the RNA sequence of interest is single-stranded and is at least 8 nucleotides in length;
  wherein the steps of the method are also carried out with a second single-stranded DNA probe is at least 8 nucleotides in length and complementary to the RNA sequence of interest except for a specific single base mismatch; and
  wherein the binding of the modified *E. coli* RNase H detected in step (c) indicates whether an RNA:DNA hybrid molecule is present for the two DNA probe sequences, thereby permitting detection of single base mismatches in RNA.

14. The method of claim 1 where the DNA probe is labeled.

15. The method of claim 1 where step (c) comprises a protection assay.

16. The method according to claim 1 where the modified *E. coli* RNase H is labeled.

17. The method according to claim 4 where step (c) comprises removing unbound modified *E. coil* RNase H and analyzing whether the modified *E. coli* RNase H appeared to be bound to the solid support.

18. The method according to claim 17 wherein multiple defined DNA probes are linked to the solid support.

19. The method of claim 17 where the DNA probe is linked to a solid support and the modified *E. coli* RNase H is labeled.

20. The method of claim 17 where the solid support is a DNA chip.

21. The method of claim 17 where analyzing whether the modified *E. coli* RNase H appeared to be bound to the solid support comprises imaging the binding of the modified *E. coli* RNase H using Surface Plasmon Resonance Imaging.

22. The method of claim 17 where the modified *E. coil* RNase H is labeled with a fluorescent tag, an alkaline phosphatase system, or a luciferase system.

23. The method according to claim 17 wherein the label on modified *E. coli* RNase H is a readily-assayed second protein associated with the modified *E. coli* RNase H.

24. The method of claim 1 where the DNA probe contains degradation-resistant phosphorothioate linkages in place of the typical phosphate linkages.

* * * * *

SEQUENCE LISTING

```
<160> NUMBER OF SEQ ID NOS: 7

<210> SEQ ID NO 1
<211> LENGTH: 155
<212> TYPE: PRT
<213> ORGANISM: Escherichia coli

<400> SEQUENCE: 1

Met Leu Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly Arg Glu
            20                  25                  30

Lys Thr Phe Ser Ala Gly Tyr Thr Arg Thr Thr Asn Asn Arg Met Glu
        35                  40                  45

Leu Met Ala Ala Ile Val Ala Leu Glu Ala Leu Lys Glu His Cys Glu
    50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Asp Lys Lys
                85                  90                  95

Pro Val Lys Asn Val Asp Leu Trp Gln Arg Leu Asp Ala Ala Leu Gly
            100                 105                 110

Gln His Gln Ile Lys Trp Glu Trp Val Lys Gly His Ala Gly His Pro
        115                 120                 125

Glu Asn Glu Arg Cys Asp Glu Leu Ala Arg Ala Ala Ala Met Asn Pro
    130                 135                 140

Thr Leu Glu Asp Thr Gly Tyr Gln Val Glu Val
145                 150                 155

<210> SEQ ID NO 2
<211> LENGTH: 155
<212> TYPE: PRT
<213> ORGANISM: Artificial
<220> FEATURE:
<223> OTHER INFORMATION: Modified from E. coli
```

```
<400> SEQUENCE: 2

Met Leu Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly Arg Glu
            20                  25                  30

Lys Thr Phe Ser Ala Gly Tyr Thr Arg Thr Thr Asn Asn Arg Met Glu
        35                  40                  45

Leu Met Ala Ala Ile Val Ala Leu Glu Ala Leu Lys Glu His Cys Glu
    50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Asp Lys Lys
                85                  90                  95

Pro Val Lys Asn Val Asp Leu Trp Gln Arg Leu Asp Ala Ala Leu Gly
            100                 105                 110

Gln His Gln Ile Lys Trp Glu Trp Val Lys Gly His Ala Gly His Pro
        115                 120                 125

Glu Asn Glu Arg Cys Ala Glu Leu Ala Arg Ala Ala Ala Met Asn Pro
    130                 135                 140

Thr Leu Glu Asp Thr Gly Tyr Gln Val Glu Val
145                 150                 155

<210> SEQ ID NO 3
<211> LENGTH: 155
<212> TYPE: PRT
<213> ORGANISM: Artificial
<220> FEATURE:
<223> OTHER INFORMATION: Modified from E. coli

<400> SEQUENCE: 3

Met Leu Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly Arg Glu
            20                  25                  30

Lys Thr Phe Ser Ala Gly Tyr Thr Arg Thr Thr Asn Asn Arg Met Glu
        35                  40                  45

Leu Met Ala Ala Ile Val Ala Leu Glu Ala Leu Lys Glu His Cys Glu
    50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Gly Lys Lys
                85                  90                  95

Pro Val Lys Asn Val Asp Leu Trp Gln Arg Leu Asp Ala Ala Leu Gly
            100                 105                 110

Gln His Gln Ile Lys Trp Glu Trp Val Lys Gly His Ala Gly His Pro
        115                 120                 125

Glu Asn Glu Arg Cys Ala Glu Leu Ala Arg Ala Ala Ala Met Asn Pro
    130                 135                 140

Thr Leu Glu Asp Thr Gly Tyr Gln Val Glu Val
145                 150                 155

<210> SEQ ID NO 4
<211> LENGTH: 155
<212> TYPE: PRT
<213> ORGANISM: Artificial
<220> FEATURE:
```

<223> OTHER INFORMATION: Modified from E. coli

<400> SEQUENCE: 4

```
Met Thr Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly Arg Glu
            20                  25                  30

Lys Thr Phe Ser Ala Gly Tyr Thr Arg Thr Thr Asn Asn Arg Met Glu
        35                  40                  45

Leu Met Ala Ala Ile Val Ala Leu Glu Ala Leu Thr Glu His Cys Glu
50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Glu Lys Lys
                85                  90                  95

Pro Val Lys Asn Val Asp Leu Trp Gln Arg Leu Asp Leu Ala Ile Gln
            100                 105                 110

Ser His Thr Ile Gln Trp Glu Trp Val Lys Gly His Ala Gly His Pro
        115                 120                 125

Glu Asn Glu Arg Cys Ala Glu Leu Ala Arg Gln Gly Ala Asn Ser Pro
    130                 135                 140

Thr Leu Asp Asp Val Gly Tyr Leu Pro Glu Ser
145                 150                 155
```

<210> SEQ ID NO 5
<211> LENGTH: 155
<212> TYPE: PRT
<213> ORGANISM: Artificial
<220> FEATURE:
<223> OTHER INFORMATION: Modified from E. coli

<400> SEQUENCE: 5

```
Met Thr Lys Gln Val Glu Ile Phe Thr Asp Gly Ser Cys Leu Gly Asn
1               5                   10                  15

Pro Gly Pro Gly Gly Tyr Gly Ala Ile Leu Arg Tyr Arg Gly Arg Glu
            20                  25                  30

Lys Thr Phe Ser Ala Gly Tyr Thr Arg Thr Thr Asn Asn Arg Met Glu
        35                  40                  45

Leu Met Ala Ala Ile Val Ala Leu Glu Ala Leu Thr Glu His Cys Glu
50                  55                  60

Val Ile Leu Ser Thr Asp Ser Gln Tyr Val Arg Gln Gly Ile Thr Gln
65                  70                  75                  80

Trp Ile His Asn Trp Lys Lys Arg Gly Trp Lys Thr Ala Gly Lys Lys
                85                  90                  95

Pro Val Lys Asn Val Asp Leu Trp Gln Arg Leu Asp Leu Ala Ile Gln
            100                 105                 110

Ser His Thr Ile Gln Trp Glu Trp Val Lys Gly His Ala Gly His Pro
        115                 120                 125

Glu Asn Glu Arg Cys Ala Glu Leu Ala Arg Gln Gly Ala Asn Ser Pro
    130                 135                 140

Thr Leu Asp Asp Val Gly Tyr Leu Pro Glu Ser
145                 150                 155
```

<210> SEQ ID NO 6
<211> LENGTH: 468
<212> TYPE: DNA
<213> ORGANISM: Artificial

-continued

```
<220> FEATURE:
<223> OTHER INFORMATION: Modified from E. coli

<400> SEQUENCE: 6
atgacgaaac aggtggaaat cttcaccgat ggttcgtgtc tgggcaatcc aggacctggg      60
ggttacggcg ctattttacg ctatcgcgga cgcgagaaaa cctttagcgc tggctacacc     120
cgcaccacca acaaccgtat ggagttgatg gccgctattg tggccctgga ggcgttaaca     180
gagcattgcg aagtcatttt gagtaccgac agccaatatg ttcgtcaggg gatcacccag     240
tggatccata actggaaaaa gcgcggctgg aaaacggcag agaaaaagcc ggtgaaaaat     300
gtcgatctct ggcagcgcct tgacctcgca attcagagcc atacgataca gtgggagtgg     360
gttaaaggcc atgcgggaca cccggagaac gaacgttgcg cagaattggc gcgacagggt     420
gccaactccc ccacactgga cgatgtcggc tacctgcctg agagttaa                  468

<210> SEQ ID NO 7
<211> LENGTH: 468
<212> TYPE: DNA
<213> ORGANISM: Artificial
<220> FEATURE:
<223> OTHER INFORMATION: Modified from E. coli

<400> SEQUENCE: 7
atgacgaaac aggtggaaat cttcaccgat ggttcgtgtc tgggcaatcc aggacctggg      60
ggttacggcg ctattttacg ctatcgcgga cgcgagaaaa cctttagcgc tggctacacc     120
cgcaccacca acaaccgtat ggagttgatg gccgctattg tggccctgga ggcgttaaca     180
gagcattgcg aagtcatttt gagtaccgac agccaatatg ttcgtcaggg gatcacccag     240
tggatccata actggaaaaa gcgcggctgg aaaacggccg gcaaaaagcc ggtgaaaaat     300
gtcgatctct ggcagcgcct tgacctcgca attcagagcc atacgataca gtgggagtgg     360
gttaaaggcc atgcgggaca cccggagaac gaacgttgcg cagaattggc gcgacagggt     420
gccaactccc ccacactgga cgatgtcggc tacctgcctg agagttaa                  468
```